(12) United States Patent
Leroy et al.

(10) Patent No.: US 10,281,304 B2
(45) Date of Patent: May 7, 2019

(54) DEVICE AND METHOD FOR ESTIMATING A FLOW OF GAS IN AN ENCLOSURE MAINTAINED AT REDUCED PRESSURE IN RELATION TO THE GAS

(71) Applicant: Commissariat a l'energie atomique et aux energies alternatives, Paris (FR)

(72) Inventors: Arnaud Leroy, Chambery (FR); Stephane Cros, Chambery (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 640 days.

(21) Appl. No.: 14/440,264

(22) PCT Filed: Nov. 6, 2013

(86) PCT No.: PCT/EP2013/073162
§ 371 (c)(1),
(2) Date: May 1, 2015

(87) PCT Pub. No.: WO2014/072339
PCT Pub. Date: May 15, 2014

(65) Prior Publication Data
US 2015/0276443 A1    Oct. 1, 2015

(30) Foreign Application Priority Data
Nov. 6, 2012 (FR) ..................... 12 60532

(51) Int. Cl.
*G01F 1/50* (2006.01)
*G01N 15/08* (2006.01)
(52) U.S. Cl.
CPC ........... *G01F 1/50* (2013.01); *G01N 15/0826* (2013.01)
(58) Field of Classification Search
CPC ............... G01F 1/50; G01N 15/0826
(Continued)

(56) References Cited

U.S. PATENT DOCUMENTS 3,548,634 A * 12/1970 Roy .................. G01N 15/0826
73/38
5,361,625 A * 11/1994 Ylvisaker ............ G01N 15/082
73/38
(Continued)

FOREIGN PATENT DOCUMENTS

FR    2 897 434 A1    8/2007
FR    2 959 314 A1    10/2011
(Continued)

OTHER PUBLICATIONS

J. McBreen, et al., "A Method for Determination of the Permeation Rate of Hydrogen Through Metal Membranes", Journal of the Electrochemical Society, vol. 113, No. 11, pp. 1218-1222, (Jan. 1, 1991), XP008165264.
(Continued)

*Primary Examiner* — Tan T. Nguyen
(74) *Attorney, Agent, or Firm* — Oblon, McClelland, Maier & Neustadt, L.L.P.

(57) ABSTRACT

Method for estimating a gas flow in an enclosure maintained in a low pressure regimen relative to the gas, including:
measuring, as a function of time, a gas flow $J_{measurement}$ in the enclosure, and
estimating values of the parameters A and B iteratively implemented by decreasing an estimation error based on a difference between $J_{estim}(t)$ and $J_{measurement}$, and wherein, when $J_{measurement}$ corresponds to a pressure rise of the gas in the enclosure, $J_{estim}(t)$ is calculated according to the equation:

$$J_{estim}(t) = 2A \sum_{n=1}^{n\,max} \left(\frac{B}{\pi(t-OffX)}\right)^{\frac{1}{2}} \exp\left(\frac{-2(n+1)^2}{4B(t-OffX)}\right) + OffY$$

(Continued)

and when $J_{measurement}$ corresponds to a pressure decrease of the gas in the enclosure, $J_{estim}(t)$ is calculated according to the equation:

$$J_{estim}(t) = P_{init} - 2A \sum_{n=1}^{n\,max} \left(\frac{B}{\pi(t-OffX)}\right)^{\frac{1}{2}} \exp\left(\frac{-(2n+1)^2}{4B(t-OffX)}\right) + OffY$$

FIG. 1.

15 Claims, 8 Drawing Sheets

(58) Field of Classification Search
USPC .......................................... 702/47, 138, 140
See application file for complete search history.

(56) References Cited

U.S. PATENT DOCUMENTS

| | | | |
|---|---|---|---|
| 5,513,515 A * | 5/1996 | Mayer | G01N 15/0826 73/38 |
| 5,916,685 A * | 6/1999 | Frisk | B32B 27/36 428/446 |
| 6,335,202 B1 | 1/2002 | Lee et al. | |
| 6,510,746 B1 * | 1/2003 | Kotwicki | G01F 1/363 702/100 |
| 7,624,621 B2 | 12/2009 | Firon et al. | |
| 2003/0185333 A1 * | 10/2003 | Sacedon Adelantado | G01N 7/10 376/245 |
| 2004/0123646 A1 * | 7/2004 | Echigo | G01N 15/0826 73/38 |
| 2005/0092068 A1 * | 5/2005 | Ascheman | G01N 7/10 73/38 |
| 2007/0138936 A1 * | 6/2007 | Chang | H01J 61/305 313/493 |
| 2007/0186622 A1 * | 8/2007 | Firon | G01N 15/0826 73/38 |
| 2009/0133475 A1 * | 5/2009 | Glock-Jager | G01N 15/0806 73/38 |
| 2010/0223979 A1 * | 9/2010 | Ploehn | G01N 15/0826 73/38 |
| 2011/0168023 A1 * | 7/2011 | Nunes | B01D 65/003 96/4 |
| 2014/0013824 A1 * | 1/2014 | Welt | G01N 15/082 73/38 |
| 2014/0026756 A1 * | 1/2014 | Guo | B01D 53/228 96/10 |
| 2014/0223999 A1 * | 8/2014 | Graehlert | G01N 15/0826 73/38 |
| 2014/0234602 A1 | 8/2014 | Cros et al. | |
| 2016/0003726 A1 * | 1/2016 | Hara | G01N 15/0826 73/38 |

FOREIGN PATENT DOCUMENTS

| | | |
|---|---|---|
| JP | 59-15834 A | 1/1984 |
| JP | 61-25047 A | 2/1986 |
| JP | 62-119433 A | 5/1987 |
| JP | 2000-214069 A | 8/2000 |
| JP | 2012-64486 A | 3/2012 |

OTHER PUBLICATIONS

Richard Ash, et al., "Transport through a slab membrane governed by a concentration-dependent diffusion coefficient III. Numerical solution of the diffusion equation: 'early-time' and '√t' procedures", Journal of Membrane Science, vol. 180, pp. 133-146, (Jan. 1, 2000), XP055082973.

Stephane Cros, et al., "Relationship between encapsulation barrier performance and organic solar cell lifetime", Proc. of SPIE, vol. 7048, (2008).

International Search Report dated Mar. 11, 2014 in PCT/EP13/073162 Filed Nov. 6, 2013.

French Search Report dated Oct. 15, 2013 in French Application No. 12 60532 Filed Nov. 6, 2012.

Office Action dated Jun. 26, 2017 in corresponding Japanese Patent Application No. 2015-540174 (with English Translation), citing documents AO, AP, AQ, AR and AS therein, 4 pages.

* cited by examiner

DEVICE AND METHOD FOR ESTIMATING A FLOW OF GAS IN AN ENCLOSURE MAINTAINED AT REDUCED PRESSURE IN RELATION TO THE GAS

TECHNICAL FIELD

The invention relates to a device and a method for estimating at least one gas flow in an enclosure maintained in a low pressure regimen relative to the gas(es). The invention is applicable in particular for estimating the permeation, that is gas barrier properties, of a barrier layer, or barrier film.

STATE OF PRIOR ART

Some devices, such as electronic components and photovoltaic panels comprising organic materials, are particularly sensitive to oxidation induced by water and dioxygen. In order to be able to increase the lifetime of these devices, it is required to protect them at the most by using barrier films, or barrier layers, having strong water vapor and dioxygen barrier properties, for example between about $10^{-3}$ $g \cdot m^{-2} \cdot day^{-1}$ and $10^{-6}$ $g \cdot m^{-2} \cdot day^{-1}$ for Water Vapor Transmission Rate (WVTR) and in the order of $10^{-3}$ $cm^3 \cdot m^{-2} \cdot days^{-1}$ for Oxygen Transmission Rate (OTR). Such barrier films are for example "Ultra Barrier Solar Film" marketed by 3M™ Company, or X-Barrier™ film marketed by Mitsubishi Plastics' Company.

The term "barrier" means here the protection provided by the barrier material to the device with respect to the environment gases responsible for the degradation of the device. The protection of these atmosphere sensitive devices is all the more critical when it should be made with flexible materials, a fortiori when they are clear. The gas barrier properties of these layers of materials (or barrier films) can vary a lot. The conventional barrier layers, suitable for low demanding applications (for example in the food field), have WVTR between about $10^{-1}$ and $1$ $g \cdot m^{-2} \cdot days^{-1}$. The layers forming the strongest barriers to the water vapor passage have WVTR lower than about $10^{-6}$ $g \cdot m^{-2} \cdot days^{-1}$. Thus, the barrier layers do not totally prevent the gases from passing therethrough and thus have a non-zero permeation relative to gases. It is thus important to be able to measure their permeation level in order to ensure de protection of devices protected with such barrier films.

The barrier properties of these barrier layers are measured through the implementation of a permeation measurement of the layers as schematically shown in FIG. 1, enabling the gas flow transmitted by the barrier layer to be determined. A barrier layer 10 to be characterized is placed into a permeameter 11, at the interface between a first chamber 12 and a second chamber 14 (see FIG. 1, scheme a)). A measuring device 16 for detecting gases present in the second chamber 14, by measuring in particular the partial pressure of some isotopes of the gas as water vapor or oxygen, is provided in the second chamber 14. This measuring device 16 corresponds for example to a mass spectrometer. The only permeable wall between both chambers 12 and 14 is thus formed by the barrier layer 10 the permeation of which is attempted to be characterized. The first chamber 12 is filled with a target gas 18 at a controlled pressure, this gas 18 being able to be detected by the measuring device 16.

The target gas 18 is for example water vapor or oxygen or dioxygen, but the principle is true for any other gas or flavor (see FIG. 1, scheme b)). The gas 18 present in the first chamber 12 is then transmitted into the second chamber 14 by a process of solubility/diffusion through the barrier layer 10 (FIG. 1, scheme c)). Such a permeameter 11 is for example described in document U.S. Pat. No. 7,624,621 B2.

The performed permeation measurement of the barrier layer 10 gives a curve representing the change over time of the partial pressure of the gas 18 in the second chamber 14, as shown in FIG. 2. In the case of an ideal flawless permeation regimen, that is when the material of the barrier layer 10 is homogenous and the diffusion coefficient of the barrier layer 10 does not vary as a function of the target gas concentration during the measurement, this curve, corresponding to the change over time of the transfer rate of the gas 18 through the barrier layer 10, can be expressed by the Fick equation:

$$J(t) = 2P_1 S \sum_{n=1}^{\infty} \left(\frac{D}{\pi t}\right)^{\frac{1}{2}} \exp\left(\frac{-(2n+1)^2 l^2}{4Dt}\right) \quad (1)$$

with $P_1$: constant pressure of the gas 18 in the first chamber 12;
S: solubility of the barrier layer 10;
D: Diffusion coefficient of the barrier layer 10;
l: thickness of the barrier layer 10.

A parameter $C = P_1 \cdot S$ can also be used in the above equation (1).

The curve given by the equation (1) above includes two regimens: the first one, called a transient state regimen, corresponds to the rise as a function of time in the flow of the target gas 18 passing through the barrier layer 10. The second, called a steady state regimen, expresses a constant flow of the target gas 18 passing through the barrier layer 10 by solubility/diffusion. The characteristic of the target gas flow to be measured, that is the stabilized transfer rate, is obtained from a steady state regimen of the measured flow curve and corresponds to the constant value to which this curve tends. The stabilized transfer rate of the gas 18 through the barrier layer 10 can be expressed by the equation:

$$J\infty = D \cdot S \frac{\Delta P}{l} \quad (2)$$

with $\Delta P$: partial pressure difference of the gas 18 between the first chamber 12 and the second chamber 14.

The stabilized transfer rate of the gas 18 through the barrier layer 10 can also be approximated by the equation:

$$J\infty = \frac{D \cdot C}{l} \quad (3)$$

When the target gas 18 is water vapor, this stabilized transfer rate corresponds to WVTR, and when the target gas 18 is oxygen or dioxygen, this rate corresponds to OTR.

From the analysis of the first and second regimens also deduced is the characteristic time of the transient state regimen, called "Time lag". This is calculated by integrating the transfer rate curve of the gas 18 through the barrier layer 10, thus representing the cumulative amount of the gas 18 that has passed through the barrier layer 10, as a function of time. Such a curve is shown in FIG. 3. The "Time lag" parameter is thus calculated by extrapolating, at a zero amount, the linear change over time of the cumulative amount of target gas 18 in the steady state regimen.

The permeation regimen can be more complex for barrier materials including several layers such as inorganic deposits on a polymeric substrate and/or in the case of a diffusion of a gas strongly adsorbed by the barrier material (modification of the diffusion coefficient over time). In this case, the change over time of the rate transfer of such a complex permeation regimen can be expressed by representative laws which are much more complex and highly dependent on the materials being tested.

Furthermore, the implementation of such a permeation measurement raises several problems.

First, as regards the sensitivity of the measurement performed, the detection of the flow of the target gas 18 developing through the barrier layer 10 by the measuring device 16 is only possible if the signal to background noise ratio is in accordance with the detection capabilities of the measuring device 16, that is if the value of the measured signal corresponding to the gas flow 18 through the layer 10 is high enough to be distinct from the background noise present in the second chamber 14. This background noise comes from several factors:
- the minimum electronic noise, or sensitivity of the measuring device 16, such as the minimum ionization current detectable by a mass spectrometer for the isotope of the target gas considered;
- the presence of residual target gas in the second chamber 14 coming in particular from the degassing from the walls of the second chamber 14 and from the layer 10 the permeation of which is attempted to be measured (and also the filament of the mass spectrometer in the case of a measurement by such an apparatus.

A second factor complexifying such a permeation measurement is the measurement time sometimes necessary. Indeed, materials having high barrier properties can include transient state regimens (and thus "Time lags") which are particularly lengthy, that can range up to several months.

Finally, a third factor complexifying the implementation of such a measurement is the reliability of the measurement performed. Indeed, the permanent flow characteristic of the target gas measured, that is the transfer rate, can be readily truncated if its reading is unintentionally performed in an anticipated way, before the steady state regimen is reached.

These drawbacks are also found when a measurement of a gas flow is desired to be performed in an enclosure maintained in a low pressure regimen relative to the gas(es) to be measured, regardless of whether this flow corresponds to a rise in pressure of the target gas in the enclosure or to a decrease in the residual pressure of the gas within the enclosure (corresponding for example to a degassing in the enclosure, that is to the background noise).

DISCLOSURE OF THE INVENTION

One purpose of the present invention is to provide a method and a device allowing the change over time of one or several gas flow(s) in an enclosure, or volume, maintained in a low pressure regimen relative to the gas(es) measured, to be reliably simulated and with a shortened time. One purpose of the present invention is also to be able to perform an estimation of a permeation of a barrier layer by making this measurement more sensitive, more reliable and with a shortened time with respect to that necessary to devices and methods of prior art for measuring a permeation for estimating permeation properties of the barrier layer.

For this, the present invention provides a method for estimating at least one gas flow in an enclosure maintained in a low pressure regimen relative to the gas, including at least:
- measuring, as a function of time, a gas flow $J_{measurement}$ in the enclosure maintained in a low pressure regimen relative to the gas, and
- estimating values of parameters A and B iteratively implemented by decreasing an estimation error based on a difference between an estimation of the gas flow $J_{estim}$ (t) and the measured gas flow $J_{measurement}$, and wherein when the measured gas flow $J_{measurement}$ corresponds to a pressure rise of the gas in the enclosure, the estimation of the gas flow $J_{estim}(t)$ is calculated according to the equation:

$$J_{estim}(t) = 2A \sum_{n=1}^{n\,max} \left(\frac{B}{\pi(t - \mathit{OffX})}\right)^{\frac{1}{2}} \exp\left(\frac{-(2n+1)^2}{4B(t - \mathit{OffX})}\right) + \mathit{OffY}$$

and when the measured gas flow $J_{measurement}$ corresponds to a pressure decrease of the gas in the enclosure, the estimation of the gas flow $J_{estim}(t)$ is calculated according to the equation:

$$J_{estim}(t) = P_{init} - 2A \sum_{n=1}^{nmax} \left(\frac{B}{\pi(t - \mathit{OffX})}\right)^{\frac{1}{2}} \exp\left(\frac{-(2n+1)^2}{4B(t - \mathit{OffX})}\right) + \mathit{OffY}$$

with OffX and OffY: relative integers;
$P_{init}$: initial value of a measured partial pressure of the gas in the enclosure;
$n_{max}$: integer higher than or equal to 1.

The method according to the invention enables the gas flow within the enclosure to be characterized without necessarily having to wait for the steady state regimen of this flow to deduce therefrom a value of the parameters A and B which enable this gas flow to be characterized. Moreover, the estimation reliability of this gas flow is improved because it is no longer possible to unintentionally truncate the permanent flow characteristic of the target gas being measured, that is the transfer rate, before the steady state regimen is reached. The estimation of the values of the parameters A and B is iteratively performed by approaching at best the estimation $J_{estim}(t)$ of the measurement of the gas flow performed for $J_{measurement}$.

The gas flow is modeled by an equation expressing $J_{estim}(t)$ and having properties similar to the Fick equation.

When this method is applied to make an estimation of the permeation of a barrier layer, the estimated parameters A and B can in particular be used to calculate the diffusion coefficient and/or solubility and/or transfer rate and/or Time Lag of the barrier layer.

Because the enclosure is maintained in a low pressure regimen relative to the gas, this low pressure regimen is thus maintained permanently (dynamic system) and the change over time of the partial pressure of the target gas within the enclosure thus corresponds to a balance between the system making this low pressure regimen, such as a pumping system (for example through the use of a vacuum pump or a neutral gas flow) and the target gas flow of the enclosure. The pumping ability can thus be considered as constant whatever the partial pressure of target gas. Thus, the change over time of the partial pressure can be considered as being that of the target gas flow. This can be checked for insofar as the system making the low pressure regimen, such as the pumping system, is stabilized and the change over time of the partial pressure of target gas is unlikely to alter the pumping speed. For example, in the case of the use of a pumping system of the target gas through vacuum, this can be checked if the nominal operating speed of the pump is met and the pressure in the enclosure does not exceed about $10^{-5}$ mbar.

The flows can be expressed in $cm^3 \cdot day^{-1}$ for gases (or in $gram \cdot day^{-1}$ for water). In the case where the expressed flow is that of a permeation measurement, the flow value can be normed by the film area measured (for example in $cm^3 \cdot day^{-1} \cdot m^{-2}$).

The gas may be selected from water vapor, oxygen, dioxygen, one of water or oxygen isotopes, helium, hydrogen, or a mixture of at least two of said gases.

Estimating the values of the parameters A and B may include at least the implementation of the following steps of:
$a_1$) choosing initial values of the parameters A and B;
$b_1$) calculating the estimation of the gas flow $J_{estim}(t)$;
$c_1$) calculating the estimation error;
$d_1$) when the estimation error is positive, decreasing the value of the parameter A and/or the value of the parameter B, and when the estimation error is negative, increasing the value of the parameter A and/or the value of the parameter B;

and wherein the implementation of steps $b_1$) to $d_1$) is successively repeated several times until a stabilization of the estimated values of the parameters A and B is achieved.

Step $c_1$) may include the implementation of the following steps of:
dividing $J_{estim}(t)$ and $J_{measurement}$ into several parts such that each of these parts corresponds to $J_{estim}(t)$ and $J_{measurement}$ for a time interval distinct from the time intervals of the other parts;
for each of the parts of $J_{estim}(t)$ and $J_{measurement}$, calculating a parameter $$ErrorJ_{part\_i} = \int_{t \in part\_i} (J_{estim}(t) - J_{measurement}),$$

with part_i corresponding to the time interval of the corresponding parts of $J_{estim}(t)$ and $J_{measurement}$;
calculating the parameters ErrorA and ErrorB, corresponding to the estimation errors of the parameters A and B respectively and forming together the estimation error, each of the parameters ErrorA and ErrorB being equal to a linear combination of the parameters ErrorJ$_{part\_i}$;
and wherein step $d_1$) is implemented such that:
when the value of the parameter ErrorA is positive, the value of the parameter A is decreased;
when the value of the parameter ErrorA is negative, the value of the parameter A is increased;
when the value of the parameter ErrorB is positive, the value of the parameter B is decreased;
when the value of the parameter ErrorB is negative, the value of the parameter B is increased.

In this case, some parts of the curves of the gas flow measured and of the estimation of the gas flow which are only relevant for one of the parameters A and B may not be taken into account for the estimation of the other of the parameters A and B.

A stabilization of the values of the parameters A and B may be achieved when the values of the parameters A and B include at least first six digits, in scientific notation, identical to those of the values of the parameters A and B obtained during a previous implementation of steps $b_1$) to $d_1$).

The values of the parameters A and B may be decreased or increased by a variable pitch the value of which depends on previous decreases or increases of the values of the parameters A and B. Thus, it is possible to shorten the time of implementation of the method to obtain estimations of the values of the parameters A and B.

The estimation of the values of the parameters A and B may be implemented several times by considering, at each of these estimations, different values of the parameter OffX and/or the parameter OffY, and wherein final values of the parameters A and B are chosen as being those for which a global error between the measured gas flow $J_{measurement}$ and the estimation of the gas flow $J_{estim}(t)$ is minimum among all the steps of estimating the values of the parameters A and B implemented. An offset can thus be readily corrected, in X (abscissa) and/or in Y (ordinate) between the curve representing the estimation of the gas flow and the curve representing the gas flow measured.

When a global error between the measured gas flow $J_{measurement}$ and the estimation of the gas flow $J_{estim}(t)$ reaches a minimum value at an instant $t_x$ and is higher than this minimum value after $t_x$ (for example at least 10% higher during at least 5% of the measurement time), a new estimation of values of parameters $A_x$ and $B_x$, corresponding to the parameters A and B for $t > t_x$, is implemented, wherein the values of the parameters $A_x$ and $B_x$ are iteratively estimated by decreasing an estimation error based on a difference, for $t > t_x$, between an estimation of the gas flow $J_{estim\_X}(t)$ calculated based on the estimated values of the parameters $A_x$ and $B_x$ and the measured gas flow $J_{measurement}$ from which is subtracted the estimation of the gas flow $J_{estim}(t)$ for $t < t_x$, with X an integer higher than 1, and wherein the previously calculated parameters A and B are designated $A_1$ and $B_1$.

The estimation of the values of the parameters A and B may be implemented several times, which enables complex permeation regimens to be described in a universal manner without resorting to particular models for each material. A population of parameters (A; B) is thus determined.

The enclosure maintained in a low pressure regimen relative to the gas may correspond to a second chamber of a permeameter which further comprises a first chamber and a measurement device for measuring the gas present in the second chamber, the first and second chambers being separated from each other by a barrier layer having a permeation relative to the gas, and wherein the measured gas flow $J_{measurement}$ is obtained from a measurement of the change over time of the partial pressure of the gas in the second chamber. The permeation measurement performed may correspond to the measurement of WVTR or OTR of the barrier layer.

It is possible to determine the gas flow $J_{measurement}$ measured from the measurement of the partial pressure and technical characteristics of the permeameter.

For example, when the measuring device is a mass spectrometer, the knowledge of the relationship between the ionization current of the spectrometer and the partial pressure of the target gas, or a calibration of the relationship target gas partial pressure/target gas flow, enables the measurement of the gas flow to be determined.

During the implementation of the steps of measuring the gas flow $J_{measurement}$ and estimating the values of the parameters A and B, the barrier layer may be saturated with gas, and the measured gas flow $J_{measurement}$ may correspond to a pressure decrease of the gas in the second chamber of the permeameter.

The method may further include, after estimating the values of the parameters A and B, calculating a stabilized gas flow $J\infty$ such that $J\infty = A \cdot B$ or, when an estimation of the values of the parameters $A_x$ and $B_x$ is implemented, calculating stabilized gas flows $J\infty_x$ such that $J\infty_x = A_x \cdot B_x$. A total stabilized gas flow may be calculated and correspond to the sum of $J\infty$ and of $J\infty_x$.

The invention also relates to a method for estimating a permeation of a barrier layer relative to at least one gas, wherein the barrier layer separates a first chamber from a second chamber of a permeameter, including at least:
- depressurizing the first chamber and the second chamber relative to the gas;
- firstly implementing a method for estimating a gas flow as previously described, such that the measured gas flow, designated $J_{degas\_measurement}$ corresponds to a pressure decrease of the gas in the second chamber;
- calculating an estimation of a gas flow $J_{degas\_estim}(t)$ from the last values of the parameters A and B previously estimated during the first implementation of the method for estimating a gas flow;
- introducing the gas into the first chamber such that the partial pressure of the gas in the first chamber is higher than that in the second chamber;
- secondly implementing a method for estimating a gas flow such as previously described such that the measured gas flow $J_{measurement}$ corresponds to a pressure rise of the gas in the second chamber, and during which the estimation of the values of the parameters A and B is performed by decreasing the estimation error based on a difference between an estimation of the gas flow $J_{perm\_estim}(t)$ and another gas flow $J_{perm\_measurement}$ such that $J_{perm\_measurement} = J_{measurement} - J_{degas\_estim}(t)$. This method allows in this case, from the parameters A and B estimated during an estimation of the background noise in the second chamber (corresponding to $J_{degas\_estim}(t)$), the permeation of the barrier layer to be directly estimated from these parameters.

Thus, this method enables the change over time of the background noise to be efficiently simulated before performing the permeation measurement of the barrier layer. Indeed, during the first implementation of the method for estimating the gas flow, this gas flow corresponds to a measurement of a background noise in the second chamber (corresponding to the gas flows from the walls of the second chamber, from the different degassings of the measuring device as well as from the degassing of the barrier layer). During the second implementation of the method for estimating the gas flow, the measured gas flow $J_{measurement}$ thus corresponds to the sum of the flows from the background noise $J_{degas\_estim}$, that is the degassings occurring in the second chamber, and the flow from the gas permeation through the barrier layer $J_{perm\_measurement}$. By subtracting the estimation of the gas flow $J_{degas\_estim}(t)$ from the measured gas flow $J_{measurement}$ during the estimation of the parameters A and B, the measurement sensitivity of the gas flow corresponding to the permeation through the barrier layer is thus dramatically improved.

When a population of parameters (A; B) is determined, that is when the gas diffusion mechanism through the barrier layer is complex, for example in the case of a barrier layer including defects and/or having a diffusion coefficient varying as a function of the target gas concentration in the material, the method according to the invention enables the principles of the Fick equation to be applied to such complex diffusion regimens which are conventionally known not to meet the Fick's law. It is thus possible to apply the estimation method to barrier layers the permeation of which does not follow a model governed by a single permeation regimen (corresponding to a single Fick equation) but follows a model corresponding to a sum of several permeation regimens different from each other, each being able to be modeled using an equation derived from the Fick equation and the parameters A and B of which are distinct from those of other permeation regimens. In the same way, the estimation of the parameters A and B may be implemented several times in order to best describe $J_{degas\_estim}(t)$.

When a global error between the measured gas flow $J_{degas\_measurement}$ and the estimation of the gas flow $J_{degas\_estim}(t)$ is lower than the value of a first threshold $Y_{lower\_degas}$, the estimation of the gas flow $J_{degas\_estim}(t)$ is subtracted from the values of the gas flow $J_{perm\_measurement}$ measured during the second implementation of the method for estimating the gas flow and, when the global error between the measured gas flow $J_{degas\_measurement}$ and the estimation $J_{degas\_estim}(t)$ is higher than the value of a second threshold $Y_{upper\_degas}$, a last measured value of the gas flow $J_{degas\_measurement}$ or an average of several last measured values of the gas flow $J_{degas\_measurement}$ is subtracted from the values of the gas flow $J_{perm\_measurement}(t)$ measured during the second implementation of the method for estimating the gas flow.

The method may further include, after estimating the values of the parameters A and B during the second implementation of the method for estimating a gas flow, calculating a stabilized gas flow $J\infty$ such that $J\infty = A \cdot B$ or, when an estimation of values of parameters $A_x$ and $B_x$ is implemented during the second implementation of a method for estimating a gas flow, calculating stabilized gas flows $J\infty_x$ such that $J\infty_x = A_x \cdot B_x$. A total stabilized gas flow may be calculated and then correspond to the sum of $J\infty$ and $J\infty_x$.

The invention also relates to a device for estimating a permeation of a barrier layer, including means for implementing a method for estimating the permeation of the barrier layer as previously described.

There is also provided a method for estimating a permeation of a barrier layer relative to at least one gas, including at least one measurement, as a function of time, of a gas flow $J_{measurement}$ passing through the barrier layer through permeation, and an estimation of the values of parameters D and S, corresponding to a diffusion coefficient and a solubility of the barrier layer respectively, wherein the values of the parameters D and S are iteratively estimated by reducing a first estimation error based on a difference between an estimation of the gas flow $J_{estim}(t)$ calculated based on the estimated values of the parameters D and S and the measured gas flow $J_{measurement}$.

BRIEF DESCRIPTION OF THE DRAWINGS

The present invention will be better understood upon reading the description of exemplary embodiments given by way of purely indicating and in no way limiting purposes making reference to the appended drawings wherein.

Identical, similar or equivalent parts of the different figures described hereinafter bear the same reference numerals so as to facilitate switching from one figure to the other.

Different parts shown in the figures are not necessarily drawn at a uniform scale, for the figures to be more legible.

The different possibilities (alternatives and embodiments) should be understood as being non-exclusive from each other and can be combined between them.

DETAILED DISCLOSURE OF PARTICULAR EMBODIMENTS

Figure 4:
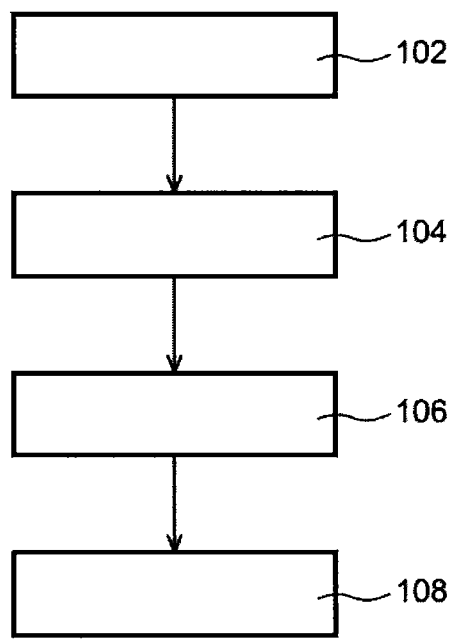
FIG. 4 shows different steps of a method for estimating the permeation of a barrier layer, object of the present invention, according to a particular embodiment.

The implementation of a method for estimating the permeation of a barrier layer 10, or barrier film, having in particular barrier properties relative to one or more gases is described according to a particular embodiment. The gas(es) considered here is (are) for example water vapor, dioxygen, one of the water or oxygen isotopes, helium, hydrogen or a mixture of at least two of these gases. This method is implemented using in particular a permeameter 11 as previously described in connection with FIG. 1. The different steps of this method are shown in FIG. 4 as a diagram.

A first step of this method is to calculate an estimation of the change over time of the background noise in the detection enclosure of the permeameter 11, that is in the second chamber 14 of the permeameter 11 (step 102). This estimation of the background noise is to estimate the change over time of the gas flow in the enclosure formed by the second chamber 14 and which corresponds to a pressure decrease of the gas in the enclosure. Indeed, the degassing of the walls of the second chamber 14 and of the barrier layer 10 to be characterized is gradually decreasing and varies over time from the moment when the second chamber 14 is maintained in a low pressure regimen relative to the target gas, corresponding for example to vacuumizing the second chamber 14. The estimation of the change over time of the background noise, referred to as $J_{degas\_estim}$, will thus allow, during the subsequent measurement and estimation of the gas permeation through the barrier layer 10, the component of the background noise to be known in the gas flow transmitted through the barrier layer 10 which will be measured, referred to as $J_{perm\_measurement}$, and thus in the estimation of this gas flow, referred to as $J_{perm\_estim}(t)$.

Figure 1:
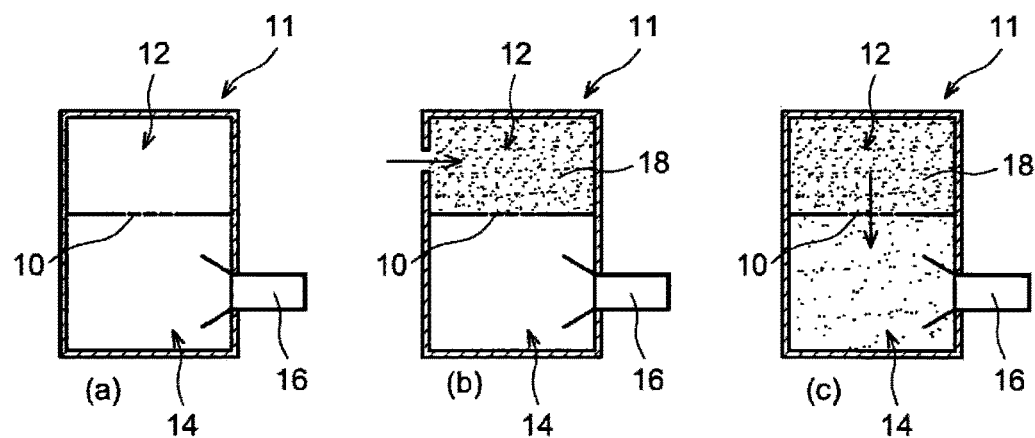
FIG. 1 shows a device and a method for measuring a permeation of a barrier layer.

For estimating $J_{degas\_estim}$, the barrier layer 10 to be characterized is provided at the interface between the first chamber 12 and the second chamber 14 of the permeameter 11, as shown in scheme a) of FIG. 1.

The chambers 12 and 14 are placed in a low pressure of the gas(es) considered.

This estimation of $J_{degas\_estim}$ is performed from measurements of the background noise, called $J_{degas\_measurement}$. In parallel to the measurement of $J_{degas\_measurement}$, calculations are thus performed to estimate $J_{degas\_estim}$. These calculations are iteratively performed by attempting to be as close as possible to the estimation $J_{degas\_estim}$ of the measurement $J_{degas\_measurement}$.

The background noise related to the degassing in the second chamber 14 of the permeameter 11 can correspond to a degassing curve obeying a slightly modified Fick equation. Indeed, the unmodified Fick equation describes an upflow, corresponding to the flow of the gas 18 passing through the barrier layer 10, and corresponds to the previously indicated equation (1). The degassing curve corresponding to the background noise is a flow decreasing with time which is expressed by the following equation (3):

$$J_{degas}(t) = P_{init} - 2C \sum_{n=1}^{\infty} \left(\frac{D}{\pi \cdot t}\right)^{\frac{1}{2}} \exp\left(\frac{-(2n+1)^2 l^2}{4D \cdot t}\right) \quad (4)$$

with I: constant;

$P_{init}$: initial value of a partial pressure of the gas 18 in the second chamber 14;

C: parameter proportional to the solubility S of the barrier layer 10;

D: diffusion coefficient of the barrier layer 10.

In order to dispense with the constant I, the above equation (4) can be written as:

$$J_{degas}(t) = P_{init} - 2A \sum_{n=1}^{\infty} \left(\frac{B}{\pi \cdot t}\right)^{\frac{1}{2}} \exp\left(\frac{-(2n+1)^2 l^2}{4B \cdot t}\right) \quad (5)$$

with A and B: natural numbers such that $A = C \times I$ and $B = D/I^2$.

Figure 5:
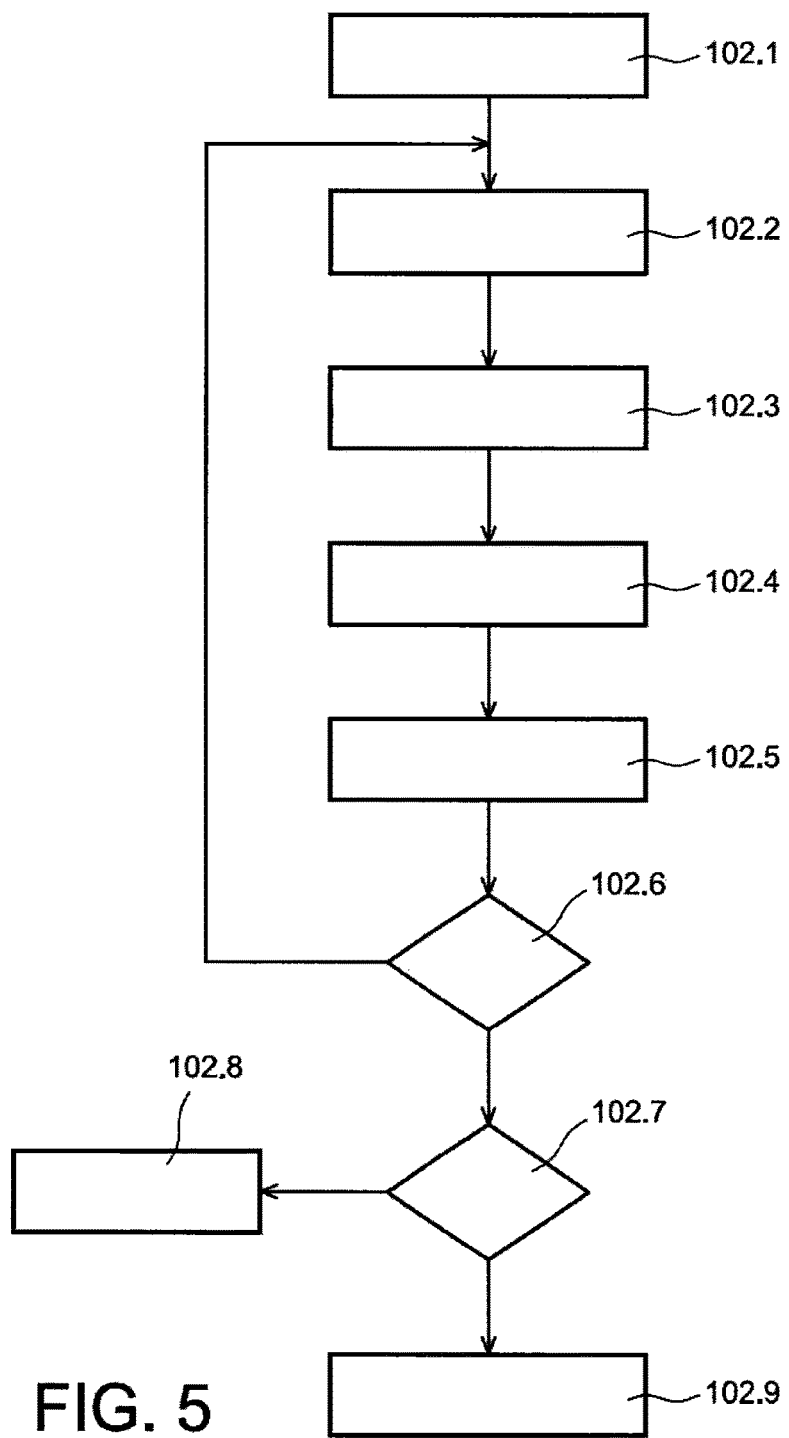
FIG. 5 shows the steps implemented for estimating a background noise in the measurement enclosure of a permeameter during a method for estimating the permeation of a barrier layer, object of the present invention, according to a particular embodiment.

The steps implemented for estimating the background noise 102 are shown in the diagram of FIG. 5.

First, initial values of the parameters A and B which will be used to calculate the estimation of the background noise (step 102.1) are defined. These initial values of the parameters A and B are for example arbitrarily chosen by the user, and correspond for example to values close to those expected and empirically known.

A vacuum, for example lower than $10^{-6}$ mbar, is made in the first chamber 12 and the second chamber 14. Then measurements of a background noise $J_{degas\_measurement}$ are performed, by the measuring device 16, in the second chamber 14 (step 102.2) corresponding to the degassing of the gas in the second chamber 14, this degassing being triggered by vacuumizing the second chamber 14. The parameters of this measurement depend in particular on the water load, the composition and structure of the barrier layer 10. The duration for implementing this measurement can range from a few minutes to several days or weeks if the barrier layer 10 and/or the second chamber 14 are strongly polluted by water. It is for example possible to measure $J_{degas\_measurement}$ at a frequency of a measuring point every two seconds, or a higher frequency if the measuring device 16 permits it.

In step 102.3, a calculation of an estimation of $J_{degas\_estim}$(t) is then performed according to the equation:

$$J_{degas\_estim}(t) = P_{init} - 2A \sum_{n=1}^{nmax} \left(\frac{B}{\pi \cdot t}\right)^{\frac{1}{2}} \exp\left(\frac{-(2n+1)^2 l^2}{4B \cdot t}\right) \quad (6)$$

The $P_{init}$ value is for example chosen as being the first measured value of $J_{degas\_measurement}$. It corresponds to the initial partial pressure of the gas considered in the second chamber 14 and is lower than the vacuum level initially made. For example, as soon as the water loaded barrier layer 10 is placed in contact with the vacuum, the barrier will begin to degas. Therefore, there will no longer be as a high vacuum as that obtained without the loaded barrier layer. The $n_{max}$ value is for example chosen as being higher than or equal to 1, for example equal to 30. Switching from step 102.2 to 102.3 is made when there are at least two measuring points, that is at least two values of $J_{degas\_measurement}$.

Then, an estimation error of $J_{degas\_estim}$ is calculated based on a difference between $J_{degas\_estim}(t)$ and $J_{degas\_measurement}$ (step 102.4). Unlike the measured background noise $J_{degas\_measurement}$ which corresponds to a finite number of measuring points obtained on a finite duration (corresponding to the duration until which the measurement is performed), the estimated background noise $J_{degas\_estim}(t)$ can be calculated on any duration because it is expressed as a mathematical function. To make the calculation of the estimation error of $J_{degas\_estim}(t)$, the function $J_{degas\_estim}(t)$ is considered on a range of values of t corresponding to the duration of the measurement of $J_{degas\_measurement}$ previously made. A comparison of both curves corresponding to $J_{degas\_measurement}$ and $J_{degas\_estim}(t)$ can thus be made on a same time interval.

Because of the specificities of the Fick equation (1) which are also applied to the preceding equations (4) to (6) modeling the change over time of the background noise, the parameter A can be considered as only varying the amplitude of the curve corresponding to $J_{degas\_estim}(t)$, whereas B can be considered as varying the "spread" of this curve along the time axis. Given that the degassing corresponding to the background noise is always decreasing, the estimation error of the value of the parameter A can be obtained by considering the end of the measurement and estimation curves of the background noise, whereas that of the B value can be visible with little interference of A at the start of the measurement and estimation curves of the background noise.

In order to be able to calculate independently the estimation errors of the parameters A and B, the curves corresponding to $J_{degas\_estim}(t)$ and $J_{degas\_measurement}$ will be divided into several parts along the time axis. For each of these parts, an error parameter is calculated such that:

$$ErrorJ_{degas\_part\_i} = \int_{t \in part\_i} (J_{degas\_estim}(t) - J_{degas\_measurement}) \quad (7)$$

with part_i corresponding to the time interval of the parts corresponding to $J_{degas\_estim}(t)$ and $J_{degas-measurement}$. The calculation of thus integral is performed by considering the measuring points of $J_{degas\_measurement}$ obtained on the time interval corresponding to the considered part of the curves, the values of $J_{degas\_estim}(t)$ being calculated for different values of t corresponding to the instants at which the measuring points of $J_{degas\_measurement}$ have been obtained.

The error of each of these parts corresponds to the area lying between the measurement and estimation curves at each of these parts.

The error is positive when this area is above the measurement curve (in the case of an overestimation of the background noise), and negative when this area is below the measurement curve (in the case of an underestimation of the background noise).

These different integrals are then combined between them to calculate estimation errors of the parameters A and B.

Figure 6:
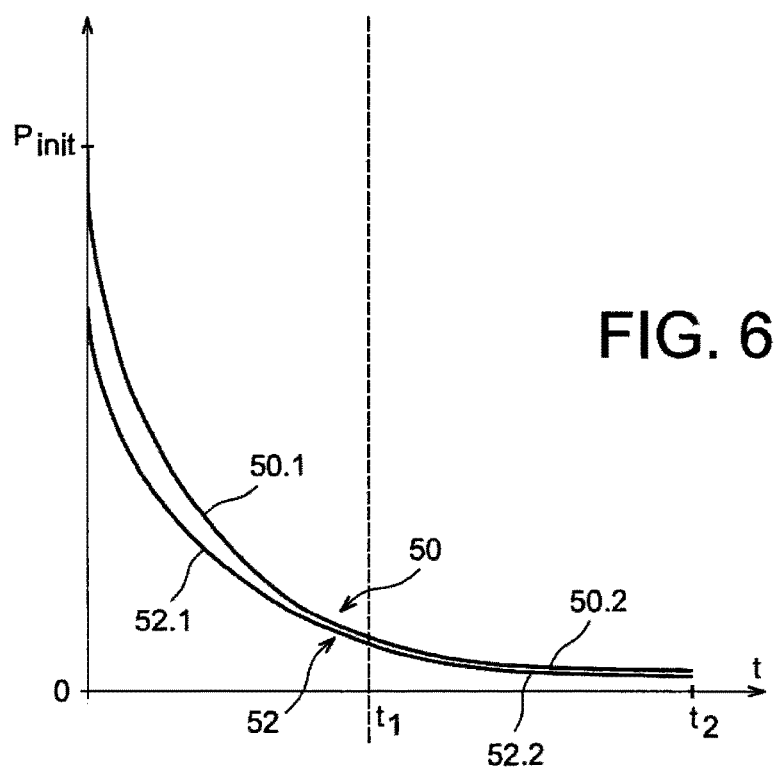
FIG. 6 shows curves corresponding to the measured background noise and the estimated background noise during a method for estimating the permeation of a barrier layer, object of the present invention, according to a particular embodiment.
Figure 2:
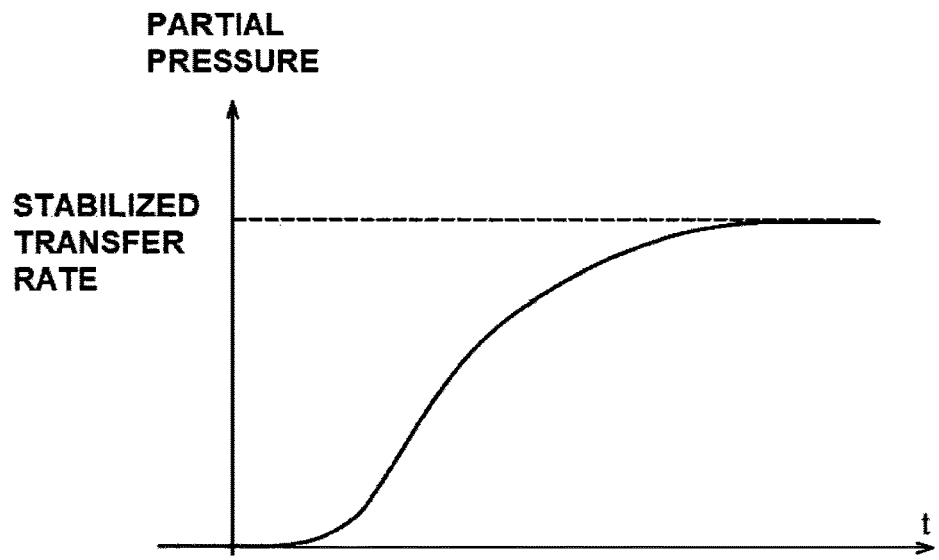
FIGS. 2 and 3 show measurement curves of the change over time of a gas partial pressure and a cumulative gas amount as a function of time through a barrier layer.
Figure 3:
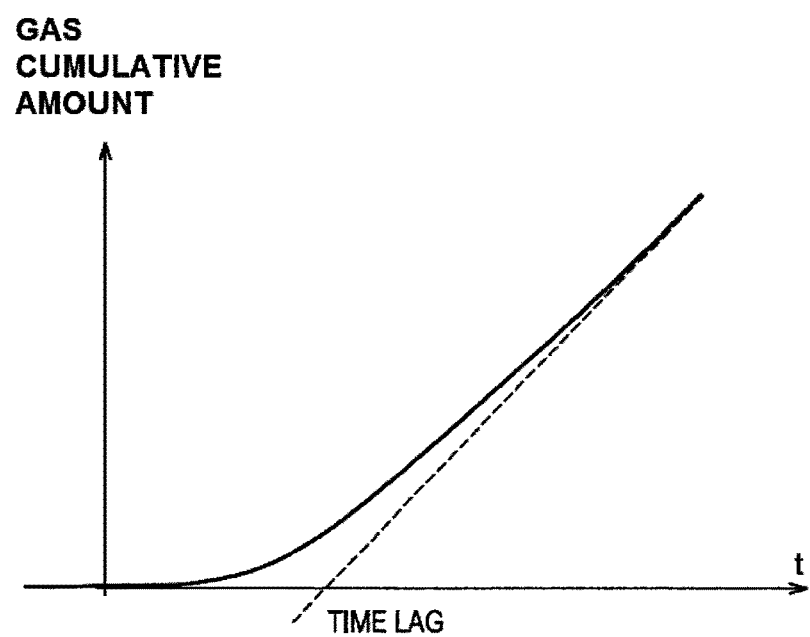

A first possibility to calculate the estimation errors of the parameters A and B can be to consider the measurement and estimation curves of the background noise as being each formed by two distinct parts by "intersecting" the time axis into two. In the example of FIG. 6, the curve 50 represents the measured background noise $J_{degas\_measurement}$ and includes a first part 50.1 for $t \in [0; t_1]$ and a second part 50.2 for $t \in [t_1; t_2]$. The curve 52 represents the estimation of the background noise $J_{degas\_estim}(t)$ and includes a first part 52.1 for $t \in [0; t_1]$ and a second part 52.2 for $t \in [t_1; t_2]$. $t_1$ and $t_2$ values are for example such that $t_2$ is equal to about twice $t_1$, the interval $[0; t_2]$ corresponding for example to the total duration during which the background noise has been measured. The estimation error on each of both parts is then calculated according to the above equation (7), by calculating the integral of the difference between the estimation and the measurement of the background noise. The errors of the parameters A and B are then calculated such that:

$$ErrorB = \int_{t \in [0;t1]} (J_{degas\_estim}(t) - J_{degas\_measurement}) = ErrorJ_{degas\_part\_1} \quad (8)$$

$$ErrorB = \int_{t \in [t1;t2]} (J_{degas\_estim}(t) - J_{degas\_measurement}) = ErrorJ_{degas\_part\_2} \quad (9)$$

A second possibility to calculate ErrorA and ErrorB can be to consider the measurement and estimation curves as being each formed by four distinct parts: a first part of each of both curves on an interval $t \in [0; t_1]$, a second part of each of both curves on an interval $t \in [t_1; t_2]$, a third part of each of the curves on an interval $t \in [t_2; t_3]$, a fourth part of each of the curves on an interval $t \in [t_3; t_4]$. Here, $t_4$ corresponds to the end of the measurement of the background noise, and these four parts each span around one quarter of this total duration. The error on each of these four parts is then calculated according to the above equation (7), by calculating the integral of the difference between the estimation and the measurement of the background noise. The errors of the parameters A and B are then calculated by combining the different errors calculated for the different parts of the curves such that for example:

$$ErrorB = \int_{t\in[0;t1]} (J_{degas\_estim}(t) - J_{degas\_measurement}) + \qquad (10)$$

$$2\int_{t\in[t1;t2]} (J_{degas\_estim}(t) - J_{degas\_measurement}) +$$

$$3\int_{t\in[t2;t3]} (J_{degas\_estim}(t) - J_{degas\_measurement})$$

$$ErrorA = 2\int_{t\in[t3;t4]} (J_{degas\_estim}(t) - J_{degas\_measurement}) + \qquad (11)$$

$$\int_{t\in[t2;t3]} (J_{degas\_estim}(t) - J_{degas\_measurement})$$

There is thus in this case:

$ErrorB = ErrorJ_{degas\_part\_1} + 2\cdot ErrorJ_{degas\_part\_2} + 3\cdot ErrorJ_{degas\_part\_3}$, and $ErrorA = 2\cdot ErrorJ_{degas\_part\_4} + ErrorJ_{degas\_part\_3}$.

A third possibility to calculate the estimation errors of the parameters A and B can be to consider the measurement and estimation curves as being each formed by four distinct parts: a first part of each of both curves on an interval $t\in[t_1; t_2]$, a second part of each of both curves in an interval $t\in[t_2; t_3]$, a third part of each of the curves on an interval $t\in[t_3; t_4]$, and a fourth part of each of the curves on an interval $t\in[t_4; t_5]$. Here, $t_5$ corresponds to the end of the measurement of the background noise and $t_1$ corresponds to the t value for example from which the values of $J_{degas\_measurement}$ are lower than the sum of the first measured value of $J_{degas\_measurement}$ and twice the standard deviation of the first 30 measured values of $J_{degas\_measurement}$. The time intervals of these four parts correspond to durations approximately equal to each other. The error of each of these four parts is then calculated as set out above according to the equation (7), by calculating the integral of the difference between the estimation and the measurement of the background noise.

The errors of the parameters A and B are then calculated by combining the different errors calculated for the different parts of the curves such as for example:

$$ErrorB = \int_{t\in[t1;t2]} (J_{degas\_estim}(t) - J_{degas\_measurement}) + \qquad (12)$$

$$2\int_{t\in[t2;t3]} (J_{degas\_estim}(t) - J_{degas\_measurement}) +$$

$$3\int_{t\in[t3;t4]} (J_{degas\_estim}(t) - J_{degas\_measurement})$$

$$ErrorA = 2\int_{t\in[t4;t5]} (J_{degas\_estim}(t) - J_{degas\_measurement}) + \qquad (13)$$

$$\int_{t\in[t3;t4]} (J_{degas\_estim}(t) - J_{degas\_measurement})$$

The three calculation possibilities of the errors of the parameters A and B set out above are exemplary embodiments, and other linear combinations of the errors of the different parts of the measurement and estimation curves of the background noise can be made for calculating ErrorA and ErrorB. It is also possible to take parts of the curves partly overlapping with each other into account.

Once the calculations of the estimation errors of the parameters A and B are made, the values of the parameters A and B are modified by adding to or subtracting from them a respective "pitch", as a function of the value, and in particular of the sign, of the estimation error of the parameter (step 102.5). If the error of the parameter (ErrorA or ErrorB) is negative, this means that the estimated value of the parameter is too small, and thus that the estimated value of the corresponding parameter should be increased. Conversely, if the error of the parameter is positive, this means that the estimated value of the parameter is too high and thus that the estimated value of the parameter should be decreased. The pitch value of each parameter is for example between about $1\cdot 10^{-25}$ and $1\cdot 10^{-6}$.

In step 102.6, a stabilization of the estimation of the background noise is then assessed by analyzing the variation in the estimations of the parameters A and B with respect to the previous estimation (when this is the first estimation of the parameters A and B, steps 102.2 to 102.6 are automatically repeated). Indeed, if the values of these parameters are stabilized, this means that the model selected for the estimation (thus the values of A and B) does correspond to the measurement and thus that the estimation made of the background noise is stable. It is considered for example that the values of the parameters A and B are stabilized when the values of these parameters include at least first six digits, in scientific notation, identical to those of the values of these parameters obtained during a previous estimation. If the values of the parameters A and B are not stabilized, steps 102.2 to 102.6 are repeated until a stabilization of these parameters is achieved.

When the values of the parameters A and B are considered as being stable, the estimation of the background noise $J_{degas\_estim}(t)$ obtained from these estimated values of A and B is globally compared with $J_{degas\_measurement}$ in order to determine whether this estimation is satisfactory (step 102.7). In order to quantify the accuracy of this estimation, the latter can be defined as being the reverse of a global error between the estimated background noise $J_{degas\_estim}(t)$ and the measurement of the background noise $J_{degas\_measurement}$. Thus, the lower the calculating global error, the more accurate the estimation of the background noise. This global error can for example be defined as being the sum relating to each point of the squared difference between the measurement and the estimation such that:

$$ErrGlobJ_{degas} = \frac{1}{p}\sum_{i=1}^{p}(J_{degas\_measurement}(i) - J_{degas\_estim}(i))^2 \qquad (14)$$

with p corresponding to the number of points taken into account, for example equal to the number of measuring points of the background noise.

It is possible to reduce the offset influence along the axis Y of the measurement (offset on the axis of the pressure value) at the beginning of the measurement by calculating the global error according to the equation:

$$ErrGlobJ_{degas} = \frac{1}{p-a}\sum_{i=1}^{p}(J_{degas\_measurement}(i) - J_{degas\_estim}(i))^2 \qquad (15)$$

with a representing the start of the decrease of the signal $J_{degas\_measurement}$, for example the point from which the value of the measuring signal $J_{degas\_measurement}$ is lower than the average of the first measuring points minus twice the associated standard deviation on a sufficiently long duration, for example on about 10 measuring points.

The measurement and estimation of the background noise can be made in connection with the sensitivity desired by the operator for the measurement. The device used for the implementation of this method can in particular permanently indicate the sensitivity of the measuring apparatus at the time t by applying for example a multiplicative factor of 100 with respect to the estimated background noise.

This global error is for example calculated at the end of 10 minutes of measurement, with a duration for example lower than about 1 week.

If the matching between the estimation and the measurement of the background noise is considered as insufficient, that is the global error calculated above is higher than a threshold $Y_{upper\_degas}$ for example equal to about 15%, the operator can however start the measurement of the gas flow through the barrier layer to be characterized. The sensitivity indicated can be considered such that there is a ratio of 1/100 between the background noise measured at the time of starting the measurement and the measurement sensitivity wanted by the operator. It is also possible that the sensitivity corresponds to about 1/100 of an average of the last measuring points of the background noise corresponding for example to about 20% of the measurement if the stabilization is achieved.

A fixed value corresponding to the background noise (last measured value of the background noise or average of the last measured values of the background noise) will be subtracted from the permeation measurement performed thereafter (step 102.8).

The operator can also discontinue the estimation of the background noise at any time if he/she considers that the sensitivity corresponding to the minimum detection threshold of a stabilized value with respect to the background noise obtained at that time is sufficient for the measurement.

If the matching between the simulation and measurement of the background noise is considered as sufficient, that is if the calculated global error is lower than a threshold $Y_{lower\_degas}$, for example equal to 5%, the indicated sensitivity then considers the scattering of the measuring points of $J_{degas\_measurement}$ about the curve of $J_{degas\_estim}(t)$. Indeed, in this case, the measuring points of the degassing represent a Gaussian about an average represented by the simulated point (for the time considered). This scattering is characterized by its standard deviation. The deviation between the simulation curve of the degassing and the measured points enables the measurement curve to be obtained. Thus, a prolonged deviation (for example in the order of a few tens seconds, or one or several minutes) higher than twice the standard deviation will correspond to the signal from the sample and will thus not be attributable to a degassing phenomenon. The estimation curve $J_{degas\_estim}(t)$ could be subtracted from the permeation measurement performed thereafter (step 102.9).

For each of these possibilities, an automatic start of the measurement of the gas flow can be programmed. The operator then simply indicates the desired sensitivity for the measurement. The measurement procedure automatically starts as soon as the conditions desired by the user are met, that is when the measurement sensitivity wanted by the operator is higher than twice the standard deviation.

If the matching between the estimation and the measurement of the background noise is not considered as sufficient, that is if the global error indicated above is between $Y_{upper\_degas}$ and $Y_{lower\_degas}$, it is then possible to consider that the change over time of the background noise follows a first equation $J_{degas\_estim\_1}(t)$, based on the values of the parameters A and B calculated and referred to as $A_1$ and $B_1$, on a first range of values of t, and that this background noise also follows one or several other equations $J_{degas\_estim\_X}(t)$ adding to the first equation $J_{degas\_estim\_1}(t)$, based on parameters $A_x$ and $B_x$ different from $A_1$ and $B_1$, on one or several other ranges of values of t, with X an integer higher than 1.

Indeed, a background noise, or more generally a degassing, can include several regimens each corresponding to a Fick model (corresponding to the equation (5) above) governed by its own parameters A and B. In this case, the model of the change over time of the background noise can be expressed by the equation:

$$J_{degas\_estim\_total}(t) = \sum_{i=1}^{m} J_{degas\_estim\_i}(t) \tag{16}$$

where m is the number of degassing regimens corresponding to the background noise.

These m degassing regimens are added up. It should then be determined when the degassing regimen changes such that a new regime has to be added to $J_{degas\_estim\_total}(t)$. This moment is determined by the follow-up of the global error previously calculated. In order to best determine the sum of several degassing regimens, the global error previously described can be defined by the following equation:

$$ErrGlobJ_{degas} = \frac{1}{p}\sum_{i=1}^{p} \frac{J_{degas\_measurement}(i) - J_{degas\_estim}(i)}{J_{degas\_measurement}(i)} \tag{17}$$

To be able to obtain the parameters A and B of all the degassing regimens, the parameters of the first degassing regimen, referred to as $J_{degas\_1}$, are set when the error begins to increase. It is then possible to subtract the first degassing regimen from the measurement to make appear a new signal only depending on the next degassing regimen(s) $J_{degas\_x}$, with X an integer higher than 1. This signal could thus be processed in the same way as the measurement to extract the other degassing regimens therefrom.

The determination of $A_1$ and $B_1$, enabling $J_{degas\_1}$ to be determined, uses the estimated data just before the global error increases by more than 30% of the point considered during a long enough duration (1H30 for example, or more in the case of strong barrier properties, as one day or more). Steps 102.2 to 102.6 are implemented only from these data until stabilized values of $A_1$ and $B_1$ are obtained.

In the present case, steps similar to steps 102.1 to 102.6 can be implemented (iteratively as previously described) by subtracting the preceding degassing regimen(s) from the measurement to extract and determine the following degassing regimens.

Each of the degassing regimens is governed by its own equation (corresponding to the preceding equation (5)) and thus includes its own parameters A and B characterizing the degassing occurring in the period of the degassing regimen considered.

In step 102.5, it is possible to vary A and B for example at a constant pitch as previously described, or at a variable value pitch, that is a value multiplied by a coefficient unique to each parameter and the value of which can change according to the change over time of the error on the parameters A and B. Thus, this coefficient will be for example divided by 2 if the parameter oscillates between two values, which allows to gain in accuracy on the estimated parameter. In the same way, the coefficient will be for example increased by about 10% if the parameter changes several times at a stretch in the same direction, which enables the estimation quickness to be improved, when the values of the estimated parameters A and B are too far from the final values.

For example, at each iteration of step 102.5, the value of B can be modified by adding or subtracting a pitch ΔB and/or the value of A can be modified by adding or subtracting a pitch ΔA such that:
   if B changes twice at a stretch in the same direction, ΔB can for example be increased by 10%.
   if A changes twice at a stretch in the same direction, ΔA can for example be increased by 10%.
   Example for A:
   estimation 1 with A(1);
   if ErrorA positive, then estimation 2 with A(2)=(A1)−ΔA;
   if ErrorA still positive, then ΔA=ΔA×1.1, and estimation 3 with A(3)=A(2)−ΔA;
   if B and/or A oscillates about the same value (example: B(i)=B(i−2) and/or A(i)=A(i−2)), ΔA and/or ΔB can be divided by 2.
   Example:
   estimation 1 with B(1) and/or A(1);
   if ErrorB and/or ErrorA positive, then estimation 2 with B(2)=B(1)−ΔB and/or A(2)=A(1)−ΔA;
   if ErrorB and/or ErrorA negative, then estimation 3 with B(3)=B(2)+ΔB=B(1) and/or A(3)=A(2)+ΔA=A(1), and ΔB=ΔB/2 and/or ΔA=ΔA/2;
   in the other cases, ΔB and ΔA can remain constant.

There is no limit in the number of measuring points of the background noise that can be used to achieve the estimation of the background noise. However, in order to reduce the calculation load, it is possible to average the measuring signal about a maximum number of points (for example 2000).

Thus, during step 102, the change over time of the background noise is estimated thanks to the estimation of the values of the parameters A and B which enable $J_{degas\_estim}(t)$ to be deduced therefrom. In the embodiment described herein, the estimated values of the parameters A and B obtained during the estimation of the background noise are not used to directly deduce therefrom the stabilized transfer rate J∞ of the barrier layer 10.

The measurement of the gas flow 18 through the barrier layer 10 is then performed (step 104). The second chamber 14 being already under vacuum, the first chamber 12 of the permeameter 11 is then filled by the gas(es) 18 the permeation of which through the barrier layer 10 is desired to be measured. This measured flow, referred to as $J_{measurement}$, will be used to estimate the change over time of the gas flow related to the permeation (step 106), and it will then be possible to estimate the stabilized transfer rate expressed by the above equation (2) as well as possibly the Time lag of the barrier layer 10 (step 108).

The gas flow 18 measured through the barrier layer 10, which is directly proportional to the measurement of the partial pressure of the gas(es) in the second chamber 14, is governed by the Fick equation, corresponding to the previously mentioned equation (1). The gas flow corresponding to the permeation through the barrier layer 10 can thus be expressed by the equation:

$$J_{perm}(t) = 2C \sum_{n=1}^{\infty} \left(\frac{D}{\pi \cdot t}\right)^{\frac{1}{2}} \exp\left(\frac{-(2n+1)^2 l^2}{4D \cdot t}\right) \quad (18)$$

with l: thickness of the layer of material.

Analogously with the previously described equation (6) for the estimation of the background noise, the gas flow corresponding to the permeation through the barrier layer 10 can thus be expressed by the equation:

$$J_{perm\_estim}(t) = 2A \sum_{n=1}^{nmax} \left(\frac{B}{\pi \cdot t}\right)^{\frac{1}{2}} \exp\left(\frac{-(2n+1)^2}{4B \cdot t}\right) \quad (19)$$

with $n_{max}$: integer higher than or equal to 1, for example equal to 30.

As for the estimation of the previously described change over time of the background noise, the estimation of the change over time of the gas flow is iteratively determined by attempting to be as close as possible to the measurement estimation.

Figure 7:
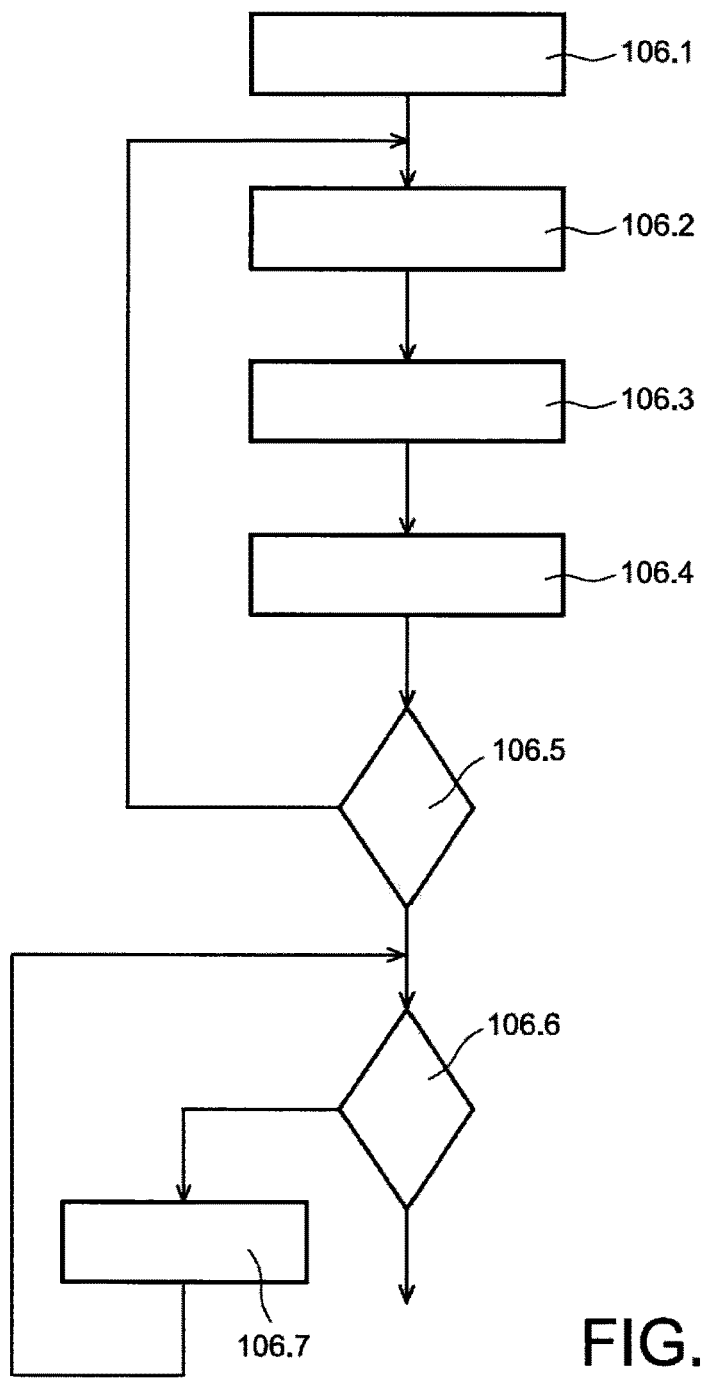
FIG. 7 shows the steps implemented for estimating the parameters D and S during a method for estimating the permeation of a barrier layer, object of the present invention, according to a particular embodiment.

The steps implemented to calculate the estimation of the gas flow $J_{perm\_estim}(t)$ are shown in the diagram of the FIG. 7.

First, initial values of the parameters A and B are defined, which will be used to calculate the estimation $J_{perm\_estim}(t)$ (step 106.1). These initial values of the parameters A and B are for example arbitrarily chosen by the user.

In step 106.2, a calculation of an estimation of the gas flow $J_{perm\_estim}(t)$ is then performed according to the equation (19) above.

Then, an estimation error of the gas flow is calculated based on a difference between the estimation of the flow $J_{perm\_estim}(t)$ and the values of the measurements of the flow $J_{perm\_measurement}(t)$ which corresponds to the measured flow $J_{measurement}$ minus the previously estimated background noise $J_{degas\_estim}(t)$ (step 106.3). This estimation error will be calculated in a substantially analogous way to the previously calculated estimation error of the background noise.

Unlike the measured flow $J_{measurement}$, and thus also unlike $J_{perm\_measurement}$, which corresponds to a finite number of measuring points obtained on a finite duration (corresponding to the duration until which the measurement is performed), the estimated gas flow $J_{perm\_estim}(t)$ can be calculated on any duration because the estimated gas flow is expressed as a mathematical function. To perform the calculation of the estimation error of the gas flow, the function $J_{perm\_estim}(t)$ is considered on a range of values of t corresponding to the duration of the measurement of the gas flow performed. A comparison of both curves corresponding to $J_{perm\_measurement}(t)$ and $J_{perm\_estim}(t)$ can thus be performed on a same time interval.

As previously described for the background noise, because of the specificities of the Fick equation, the parameter A can be considered as varying only the amplitude of the estimation $J_{perm\_estim}(t)$, whereas B can be considered as varying the "spread" of the curve along the time axis.

Different parts of $J_{perm\_measurement}$ and $J_{perm\_estim}(t)$ are considered to independently determine the estimation errors of the parameters A and B.

In order to be able to independently calculate the estimation errors of the parameters A and B, $J_{perm\_estim}(t)$ and $J_{perm\_measurement}$ are divided into several parts along the time axis. For each of these parts, an error parameter is calculated such that:

$$ErrorJ_{perm\_part\_i} = \int_{t \in part\_i} (J_{perm\_estim}(t) - J_{perm\_measurement}) \qquad (20)$$

with part_i corresponding to the time interval of the corresponding parts of $J_{perm\_estim}(t)$ and $J_{perm\_measurement}$. The calculation of this integral is performed by considering the measuring points of $J_{perm\_measurement}$ which are obtained on the time interval corresponding to the considered part of the curves, the values of $J_{perm\_estim}(t)$ being calculated for different values of t corresponding to the corresponding instants of the measuring points of $J_{perm\_measurement}$.

The error of each of these parts corresponds to the area located between the measurement and estimation curves at these parts. The error is positive when this area is above the measurement curve, and negative when this area is below the measurement curve. These different integrals are combined to each other to calculate the estimation errors of the parameters A and B.

Figure 8:
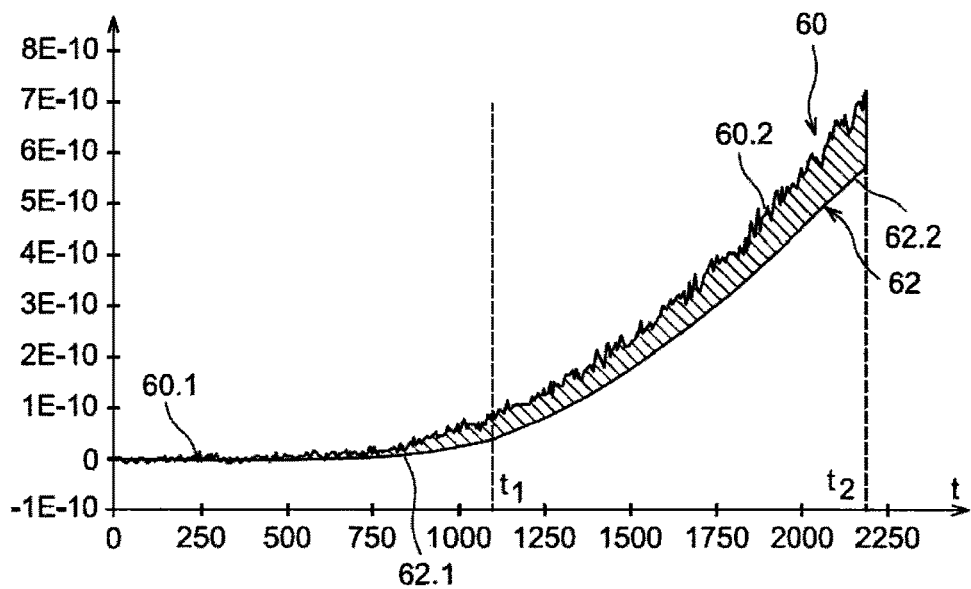
FIGS. 8 to 10 show curves corresponding to the measured gas flow and the estimated gas flow during a method for estimating the permeation of a barrier layer, object of the present invention, according to a particular embodiment.

As previously described for the estimation of the background noise, a first alternative to calculate the estimation errors of the parameters A and B can be to consider the measurement and estimation curves of the flow gas as being each formed by two distinct parts by "intersecting" the time axis into two. In the example of FIG. 8, the curve 60 represents the measured gas flow $J_{perm\_measurement}$ and includes a first part 60.1 for $t \in [0; t_1]$ and a second part 60.2 for $t \in [t_1; t_2]$. The values of $t_1$ and $t_2$ can be different from those previously described to determine the estimation error of the background noise. Curve 62 represents the estimation of the gas flow $J_{perm\_estim}(t)$ and includes a first part 62.1 for $t \in [0; t_1]$ and a second part 62.2 for $t \in [t_1; t_2]$. The values of $t_1$ and $t_2$ are for example such that $t_2$ is equal to about twice $t_1$, the interval $[0; t_2]$ corresponding to the total duration during which the gas flow has been measured. The estimation error of each of both these parts is then calculated according to the equation (15) above, by calculating the integral of the difference between the estimation and the measurement of the gas flow. The errors of the parameters A and B are then calculated such that:

$$ErrorB = \qquad (21)$$
$$\int_{t \in [0;t1]} (J_{perm\_estim}(t) - J_{perm\_measurement}) = ErreurJ_{perm\_part\_1}$$

$$ErrorA = \qquad (22)$$
$$\int_{t \in [t1;t2]} (J_{perm\_estim}(t) - J_{perm\_measurement}) = ErreurJ_{perm\_parti2}$$

Figure 9:
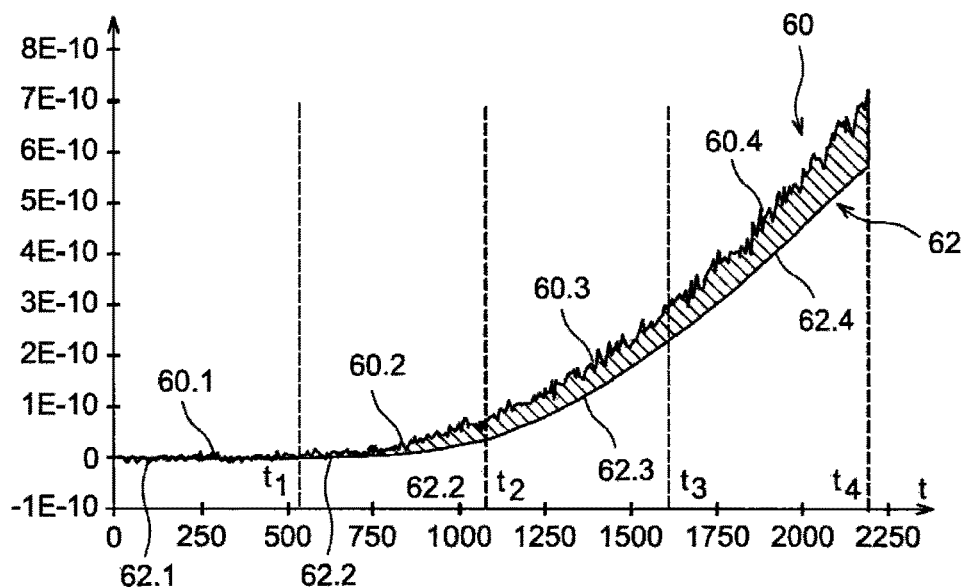

Analogously to the previously estimated background noise, a second alternative to calculate the estimation errors of the parameters A and B can be to consider the measurement and estimation curves as being each formed by four distinct parts, as shown in FIG. 9: a first part 60.1 and 62.1 of each of both curves on an interval $t \in [0; t_1]$, a second part 60.2 and 62.2 of each of both curves on an interval $t \in [t_1; t_2]$, a third part 60.3 and 62.3 of each of the curves on an interval $t \in [t_2; t_3]$, and a fourth part 60.4 and 62.4 of each of the curves on an interval $t \in [t_3; t_4]$. Here, $t_4$ corresponds to the end of the measurement of the gas flow, and these four parts each span about a quarter of this total duration. The error on each of these four parts is then calculated according to the equation (20) above, by calculating the integral of the difference between the estimation and the measurement of the gas flow. The errors of the parameters A and B are then calculated by combining the different errors calculated for the different parts of the curves such as for example:

$$ErrorB = \int_{t \in [0;t1]} (J_{perm\_estim}(t) - J_{perm\_measurement}) + \qquad (23)$$
$$2\int_{t \in [t1;t2]} (J_{perm\_estim}(t) - J_{perm\_measurement}) +$$
$$3\int_{t \in [t2;t3]} (J_{perm\_estim}(t) - J_{perm\_measurement})$$

$$ErrorA = 2\int_{t \in [t3;t4]} (J_{perm\_estim}(t) - J_{perm\_measurement}) + \qquad (24)$$
$$\int_{t \in [t2;t3]} (J_{perm\_estim}(t) - J_{perm\_measurement})$$

There is thus $ErrorB = ErrorJ_{perm\_part\_1} + 2 \cdot ErrorJ_{perm\_part\_2} + 3 \cdot ErrorJ_{perm\_part\_3}$, and $ErrorA = 2 \cdot ErrorJ_{perm\_part\_4} + ErrorJ_{perm\_part\_3}$.

In comparison with the first alternative previously set out consisting in separating the curves into two parts, a division into four parts of the measurement and estimation curves to calculate the estimation errors of the parameters A and B allows to obtain finally a lower global estimation error in particular when the measurement layer has a slight X offset, that is an offset on the time axis, with respect to the theoretical model.

Figure 10:
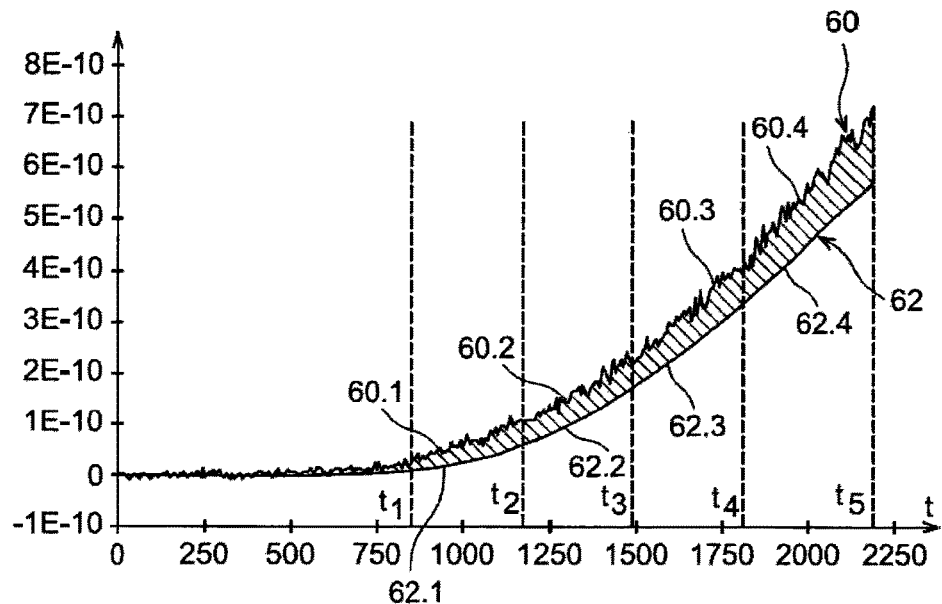

A third alternative to calculate the estimation errors of the parameters A and B can be to consider the measurement and estimation curves as being each formed by four distinct parts as shown in FIG. 10: a first part 60.1 and 62.1 of each of both curves on an interval $t \in [t_1; t_2]$, a second part 60.2 and 62.2 of each of both curves on an interval $t \in [t_2; t_3]$, a third part 60.3 and 62.3 of each of the curves on an interval $t \in [t_3; t_4]$, and a fourth part 60.4 and 62.4 of each of the curves on an interval $t \in [t_4; t_5]$. Here, $t_5$ corresponds to the end of the measurement of the gas flow and $t_1$ corresponds for example to the value of t from which the values of $J_{perm\_measurement}$ are lower than the sum of the first measured value of $J_{perm\_measurement}$ and twice the standard deviation of the first 30 measured values of $J_{perm\_measurement}$. The time intervals of these four parts correspond to durations approximately equal to each other. The error of each of these four parts is then calculated as set out above according to the equation (20), by calculating the integral of the difference between the estimation and the measurement of the gas flow. The errors of the parameters A and B are then calculated by combining the different errors calculated for the different parts of the curves such as for example:

$$ErrorB = \int_{t \in [t1;t2]} (J_{perm\_estim}(t) - J_{perm\_measurement}) + \qquad (25)$$
$$2\int_{t \in [t2;t3]} (J_{perm\_estim}(t) - J_{perm\_measurement}) +$$
$$3\int_{t \in [t3;t4]} (J_{perm\_estim}(t) - J_{perm\_measurement})$$

$$ErrorA = 2\int_{t \in [t4;t5]} (J_{perm\_estim}(t) - J_{perm\_measurement}) + \qquad (26)$$
$$\int_{t \in [t3;t4]} (J_{perm\_estim}(t) - J_{perm\_measurement})$$

In comparison with the first two alternatives previously described, this third alternative for calculating estimation errors of the parameters A and B is more versatile and is more suitable even when the measurement signal diverges from the theoretical Fick model.

The three alternatives for calculating the errors of the parameters A and B are exemplary embodiments, and other linear combinations of the errors of the different parts of the measurement and estimation curves of the gas flow can be made to calculate ErrorA and ErrorB. As for the estimation of the background noise, it is possible to consider parts of the curves partly overlapping with each other.

Once these error calculations are carried out, the values of the parameters A and B are modified by adding to or subtracting from them their respective "pitch" as a function of the value of the estimation error of the parameter (step 106.4). If the error of the parameter (ErrorA or ErrorB) is negative, this means that the estimated value of the parameter is too small, and thus that the estimated value of the corresponding parameter has to be increased. Conversely, if the error of the parameter is positive, this means that the estimated value of the parameter is too great and thus that the estimated value of the parameter should be decreased. The pitch value of each parameter is for example between about $1 \cdot 10^{-25}$ and $1 \cdot 10^{-6}$.

In step 106.5, the stabilization of the values of the parameters A and B is then assessed by analyzing the variation of the parameters A and B with respect to the previous estimation. Indeed, if the values of these parameters are stabilized, this means that the model chosen does correspond to the measurement and that the estimation performed of the gas flow is then reliable. It is considered for example that the values of the parameters A and B are stabilized when the values of these parameters include at least first six digits, in scientific notation, identical to those of the values of these parameters obtained during a previous estimation. If the values of the parameters A and B are not stabilized, steps 106.2 to 106.5 are repeated until a stabilization of these parameters is achieved. In parallel to this repetition of these steps, the measurement of the gas flow (step 104) is continued in order to continue to take the last measuring points of the gas flow into account in the estimation of the gas flow.

When the values of the parameters A and B are considered as being stable, the estimation of the gas flow $J_{perm\_estim}(t)$ obtained from the estimated values of A and B is globally compared with $J_{perm\_measurement}$ in order to determine whether this estimation is satisfactory (step 106.6). In order to quantify the accuracy of this estimation, the latter can be defined as being the reverse of a global error between the estimated gas flow $J_{perm\_estim}(t)$ and the measurement of the gas flow $J_{perm\_measurement}$. Thus, the lower the calculated global error, the more accurate the estimation of the gas flow. This global error can be defined as being the sum related to each point of the squared difference between the measurement and the estimation such that:

$$ErrGlobJ_{perm} = \frac{1}{p} \sum_{i=1}^{p} (J_{perm\_measurement}(i) - J_{perm\_estim}(i))^2 \quad (27)$$

with p corresponding to the number of points taken into account, for example equal to the number of measuring points of the gas flow.

It is possible to decrease the influence of the offset along the axis Y of the measurement (offset on the axis of the pressure value) at start of the measurement by calculating the global error according to the equation:

$$ErrGlobJ_{perm} = \frac{1}{p-a} \sum_{i=a}^{p} (J_{perm\_measurement}(i) - J_{perm\_estim}(i))^2 \quad (28)$$

with a representing the start of the increase of the signal $J_{perm\_measurement}$, for example the point from which the value of the measurement signal $J_{perm\_measurement}$ exceeds the average of the first measuring points summed to the associated standard deviation, for example on about 10 measuring points.

The device used for implementing this method can continuously display the estimated values of the parameters A, B, the global error parameter as well as the value of the stabilized flow and Time lag which are estimated based the estimated values of A and B, calculated based on the equations (29) and (30) indicated later.

If the matching between the simulation and the measurement of the gas flow is considered as sufficient, that is if the previously calculated global error is lower than a threshold $Y_{perm}$, for example between 0 and 5%, the end of the measurement of the gas flow can be anticipated, the estimated values of the parameters A and B being then considered as right. From the previously estimated parameters, the permeation of the barrier layer 10 can thus be assessed (step 108) by calculating for example the value of the stabilized gas flow $J\infty$ such that:

$$J\infty = A \cdot B \quad (29)$$

and/or the parameter TL (Time lag) such that:

$$TL = \frac{B}{6}. \quad (30)$$

Besides the $J\infty$ and TL values, it is possible to calculate the values of D (diffusion coefficient) and S (solubility) of the barrier layer from the estimated values of A and B, in accordance with the previously described equations.

If the matching between the estimation and the measurement of the gas flow is not considered as sufficient, that is if the global error indicated above is higher than a threshold $Y_{perm}$, it is then possible to consider that the gas flow follows a first equation $J_{perm\_estim\_1}(t)$, based on the values of the parameters A and B calculated and referred to as $A_1$ and $B_1$, on a first range of values of t, and that this gas flow also follows one or more other equations $J_{perm\_estim\_X}(t)$ adding up to the first equation $J_{perm\_estim\_1}(t)$, based on the parameters $A_x$ and $B_x$ different from $A_1$ and $B_1$, on a second range of values of t.

Indeed, some barrier layers can include several permeation regimens each corresponding to a Fick model governed by its own parameters A and B. In this case, the model of the gas flow through the barrier layer can be expressed by the equation:

$$J_{perm\_estim\_total}(t) = \sum_{i=1}^{m} J_{perm\_estim\_i}(t) \quad (31)$$

where m is then the number of permeation regimens of the barrier layer.

These m permeation regimens are added up. Therefore, it should be determined when the permeation regimen changes such that a new regimen has to be added to $J_{perm\_estim\_total}(t)$.

This moment is determined by following the previously calculated global error. In order to best determine the sum of several permeation regimens, the previously described global error can be defined by the following equation:

$$ErrGlobJ_{perm} = \frac{1}{p}\sum_{i=1}^{p} \frac{J_{perm\_measurement}(i) - J_{perm\_estim}(i)}{J_{perm\_measurement}(i)} \quad (28)$$

Figure 11:
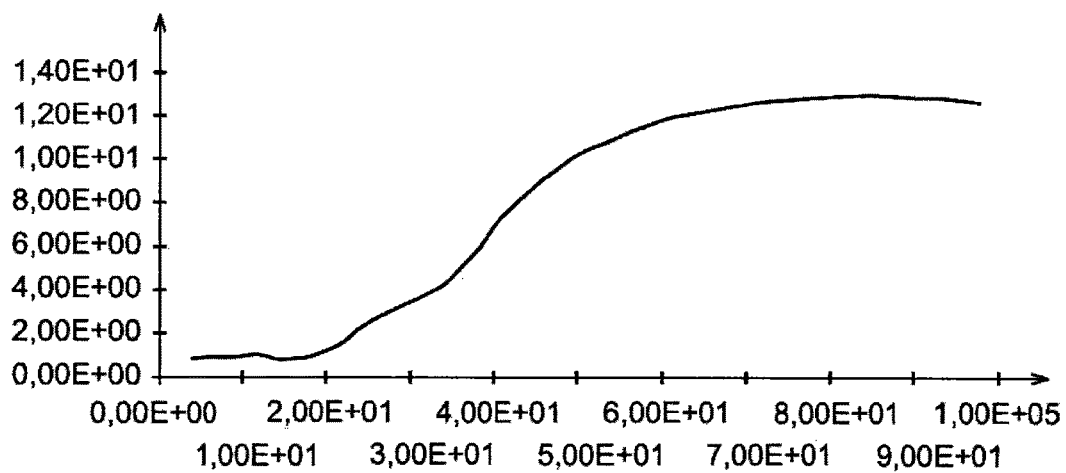
FIG. 11 shows the change over time of a global error between an estimated gas flow and a measured gas flow when this gas flow is governed by several permeation regimens.

FIG. 11 shows an exemplary change over time of the calculated global error by considering that the gas flow is governed by a single Fick equation whereas the actual permeation regimen of the barrier layer consists of the sum of several distinct permeation regimens. It can be seen in this figure that the global error is stable up to about the 20 000$^{th}$ second, and then the global error increases. This is due to the fact that the influence of a new permeation regimen is actual at that time and is added up to the first permeation regimen.

To be able to obtain the parameters A and B of all the permeation regimens, the parameters of the first permeation regimen, referred to as $J_{perm\_1}$, are set when the error starts to increase. It is thus possible to subtract the first permeation regimen from the measurement to make appear a new signal only depending on the next permeation regimen(s) $J_{perm\_x}$, with X an integer higher than 1. This signal could thus be processed in the same way as the measurement to extract the other permeation regimens therefrom.

The determination of $A_1$ and $B_1$, enabling $J_{perm\_1}$ to be determined, uses the estimated data just before the global error increases by more than 30% of the considered point for a sufficiently long duration (1H30 for example, or more in the case of strong barrier properties, as one day or more). Steps 106.2 to 106.5 are only implemented from these data until stabilized values of $A_1$ and $B_1$ are obtained.

Because in step 106.6, the global error parameter is higher than the threshold $Y_{perm}$, step 106.7 is then implemented and consists in implementing steps similar to steps 106.2 to 106.5 (iteratively as previously described) by subtracting the permeation regimen(s) from the measurement to extract and determine the next permeation regimens.

Thus, according to an exemplary gas flow curve according to several permeation regimens, it is possible to have a first permeation regimen $J_{perm\_1}$ the influence of which starts as soon as the measurement begins, a second permeation regimen $J_{perm\_2}$ the influence of which starts from the 20 000$^{th}$ second, a third permeation regimen $J_{perm\_3}$ the influence of which starts from the 30 000$^{th}$ second, and a fourth permeation regimen $J_{perm\_4}$ the influence of which here starts from the 50 000$^{th}$ second. Each of the permeation regimens is governed by its own Fick equation and thus includes its own parameters A and B characterizing the gas flow in the period of the permeation regimen considered.

When several permeation regimens are taken into consideration, step 108 then consists in calculating, from the previously described equations 24 and 25, a value of a stabilized flow J∞ and of TL for each permeation regimen.

In previously described step 106.4, it is possible to vary A and B for example according to a constant pitch, or a variable pitch, that is a value multiplied by a coefficient unique to each parameter and the value of which can change according to the change over time of the error on parameters A and B.

Thus, this coefficient will be for example divided by 2 if the parameter oscillates between two values, which allows a gain in accuracy on the estimated parameter. In the same way, the coefficient will be for example increased by about 10% if the parameter changes several times at a stretch in the same direction, which enables the quickness of the estimation start to be improved, when the estimated parameters A and B are too far from their final values.

For example, at each iteration of step 106.4 for the permeation regimen to be estimated, the value of B can be modified by adding or subtracting a pitch ΔB and the value of A can be modified by adding or subtracting a pitch ΔA such that:

if B changes two times at a stretch in the same direction, ΔB can for example be increased by 10%.
If A changes two times at a stretch in the same direction, ΔA can for example be increased by 10%.
if B and/or A oscillates about the same value, ΔA and/or ΔB can be divided by 2.

In the other cases, ΔB and ΔA can remain constant.

There is no limit in the number of measuring points of the gas flow that can be used. However, in order to reduce the calculation load, it is also possible to average a too long measuring signal about a maximum number of points (for example 2 000).

It can happen that the X (time axis) and Y (axis of the pressure measured) offsets, respectively called OffX and OffY, have an importance such that the best estimation of the gas flow corresponds to the measurement of the gas flow, and this as much for the background noise as for the permeation. To obtain the couple (offset X, offset Y) giving the lowest global error, steps 106.1 to 106.5 for the permeation and/or steps 102.1 to 102.6 for the background noise can be repeated by offsetting at each time the curve corresponding to the measurement of the gas flow of a low unit along the time axis (for example 1 second), this loop being included in another loop making such an offset of the measurement of the gas flow along the ordinate axis (for example by $1 \cdot 10^{-15}$ Pa).

In this case, the estimation of the permeation can be expressed by the following equation:

$$J_{perm\_estim}(t) = 2A\sum_{n=1}^{nmax} \left(\frac{B}{\pi(t-OffX)}\right)^{\frac{1}{2}} \exp\left(\frac{-(2n+1)^2}{4B(t-OffX)}\right) + OffY \quad (33)$$

The estimation of the background noise can be expressed by the following equation:

$$J_{deg\,as\_estim}(t) = \quad (34)$$
$$P_{init} - 2A\sum_{n=1}^{nmax} \left(\frac{B}{\pi(t-OffX)}\right)^{\frac{1}{2}} \exp\left(\frac{-(2n+1)^2}{4B(t-OffX)}\right) + OffY$$

The values of OffX and OffY considered in the estimation of the background noise can be decorrelated from those considered in the estimation of the permeation.

The algorithm of an offset correction of the estimation of the background noise and/or the permeation can correspond to:

for a ranging from -$Y_1$ to $Y_1$ per pitch of $1.10^{-15}$,
   for b ranging from -$X_1$ to $X_1$ per pitch of 1,
     Determine the estimation $J_{estim}(t)$ having the minimum error with the measurement signal $J_{measurement}$ modified by the offset a on the ordinate axis and by the offset b on the abscise axis,

```
if the global error < recorded global error, then
    recorded global error = global error,
    OffY = a
    OffX = b
End if
End for
End for
```

In this algorithm, $Y_1$ can correspond to about one tenth of the expected amplitude of the expected signal $J_{measurement}$, and $X_1$ can correspond to about one third of the expected duration of the measurement.

The estimation giving the lowest global error is then obtained by using OffY and OffX as offsets on the ordinate and abscissa axes.

This offset calculation can in particular be implemented for each permeation regimen calculated when the gas flow is estimated as corresponding to a combination of several permeation regimens.

In the previously described examples, the Fick laws are used as models for predicting the change over time of the background noise and gas flow through the barrier layer 10. Alternatively, it is possible to correlate the change over time of the background noise and gas flow to data, that is curves, for example obtained by learning or corresponding to a library provided, for example stored in a learning database. Each of these curves is for example associated with values of the parameters A and B or possibly directly to values of the parameters J∞ and TL. At each iteration of the method implemented to improve the correspondence between the measurement and the estimation (the estimation of the gas flow $J_{perm\_estim}(t)$ corresponds in this case to one of the curves of the database), the estimation error is reduced between the measurement and the estimation by choosing the curve which best corresponds to the measurements carried out. Finally, the curve of the database which best corresponds to the measurements (background noise and/or gas flow) carried out is chosen as that corresponding to the permeation model of the barrier layer 10.

The values of A and B of the chosen curve can then be considered as corresponding to those of the barrier layer 10, and from which it is possible to calculate the parameters J∞ and TL to estimate the permeation of the barrier layer 10. In the same way, several curves can be chosen in the case of a permeation governed by several permeation regimens.

In the previously described embodiment, first an estimation of the change over time of the background noise is made, and then the parameters A and B are estimated via the estimation of the change over time of the gas flow through the barrier layer 10, these estimated parameters A and B being then used to estimate the permeation of the barrier layer 10 via the calculation of J∞ and possibly of TL. Alternatively, it is possible to take both parameters A and B into account, called for example $A_{degas}$ and $B_{degas}$, estimated during the estimation of the background noise to calculate a first stabilized transfer rate, and the parameters A and B, called for example $A_{perm}$ and $B_{perm}$, estimated during the estimation of the change over time of the gas flow to calculate a second stabilized transfer rate.

In another embodiment, the method for estimating the permeation of the barrier layer 10 can consist in implementing steps 102.1 to 102.7 as previously described in order to obtain an estimation of the values of the parameters A and B via the estimation of the change over time of the background noise. From these values A and B, it is possible to directly calculate J∞ and possibly TL in order to estimate the permeation of the barrier layer 10, without implementing steps 104 to 108. This other embodiment is preferably implemented in the case of a barrier layer saturated with target gases. In this case, the first chamber 12 is for example nonexistent or the access between the first and second chambers is sealingly blocked, in order to avoid a desorption of the barrier layer off the second chamber. When several degassing regimens are taken into consideration, it is possible to calculate a value of a stabilized flow J∞ and of TL for each degassing regimen identified.

In another embodiment, the method for estimating the permeation of the barrier layer 10 can consist in implementing steps 104 to 108 as previously described without implementing step 102 beforehand, that is without making an estimation of the change over time of the background noise. In this case, the background noise is not subtracted from the measurement of the gas flow through the barrier layer 10 made. Although less accurate and having a lesser measurement sensitivity than when the background noise is taken into consideration, such an embodiment has however the advantage of being quick and suitable for a great number of barrier layers.

Whatever the embodiment considered, when several permeation regimens and/or several degassing regimens are considered, it is possible to make the calculation of a stabilized gas flow $J∞_1$ such that $J∞_1 = A_1 \cdot B_1$ and/or the calculation of stabilized gas flows $J∞_X$ such that $$J\infty_X = \sum_{i=1}^{X} A_i \cdot B_i$$

where X represents the number of the regimen the permeation of which is desired to be known, in the case of several permeation regimens which are added up.

Figure 12:
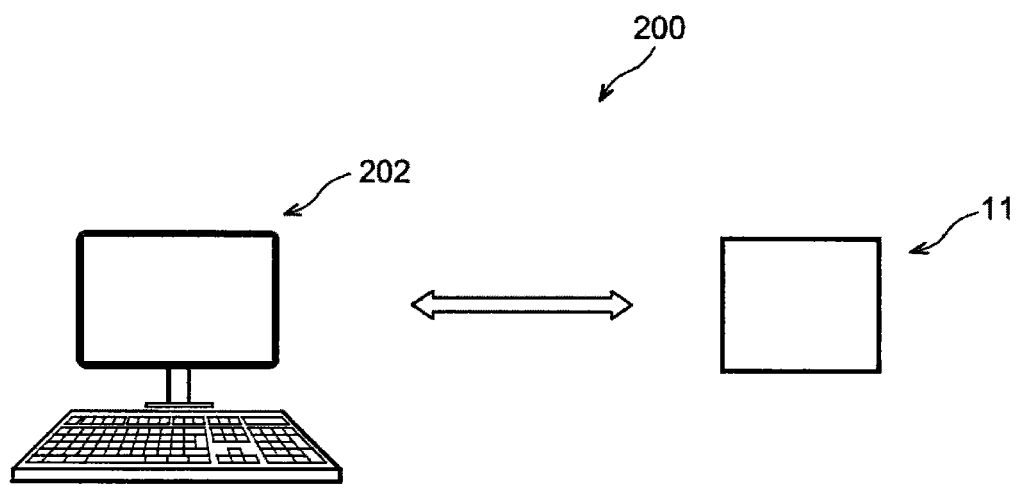
FIG. 12 shows a device for measuring a permeation, object of the present invention, according to a particular embodiment.

The method for estimating the permeation of the barrier layer 10 can be implemented by a device 200 for estimating a permeation as shown for example in FIG. 12. The device 200 includes the previously described permeameter 11, as well as one or more computers 202, or calculation units, able to form an input/output interface with the operator. The computer(s) 202 are connected to the permeameter 11 in order in particular to drive the permeameter 11, receive the measurement signals delivered by the measuring device 16 of the permeameter 11, making all the calculations of the method, etc.

The invention claimed is:

1. A method for estimating a permeation of a gas barrier layer, comprising:
   providing a permeameter including first and second chambers separated from each other by the gas barrier layer, wherein the first chamber is filled with at least one gas and the second chamber is maintained in a low pressure regimen relative to said at least one gas;
   providing a mass spectrometer in the second chamber of the permeameter;
   measuring, by the mass spectrometer, an evolution of a partial pressure of the at least one gas in the second chamber as a function of time;
   calculating, by processing circuitry, a gas flow $J_{measurement}$ in the second chamber based on the measured partial pressure of the at least one gas in the second chamber;
   estimating, by the processing circuitry, values of parameters A and B iteratively implemented by decreasing an estimation error based on a difference between an estimation of the gas flow $J_{estim}(t)$ and the measured gas flow $J_{measurement}$, wherein when the measured gas flow $J_{measurement}$ corresponds to a pressure rise of the at least one gas in the second chamber, the estimation of the gas flow $J_{estim}(t)$ is calculated according to the equation:

$$J_{estim}(t) = 2A \sum_{n=1}^{nmax} \left(\frac{B}{\pi(t-\mathit{OffX})}\right)^{\frac{1}{2}} \exp\left(\frac{-(2n+1)^2}{4B(t-\mathit{OffX})}\right) + \mathit{OffY}$$

when the measured gas flow $J_{measurement}$ corresponds to a pressure decrease of the at least one gas in the second chamber, the estimation of the gas flow $J_{estim}(t)$ is calculated according to the equation:

$$J_{estim}(t) = P_{init} - 2A \sum_{n=1}^{nmax} \left(\frac{B}{\pi(t-\mathit{OffX})}\right)^{\frac{1}{2}} \exp\left(\frac{-(2n+1)^2}{4B(t-\mathit{OffX})}\right) + \mathit{OffY}$$

and

OffX and OffY are relative integers, $P_{init}$ is an initial value of a measured partial pressure of the at least one gas in the second chamber, and $n_{max}$ is an integer higher than or equal to 1; and determining, by the processing circuitry, the permeation of the gas barrier layer based on the estimated values of the parameters A and B by calculating the difference between the estimation of the gas flow $J_{estim}(t)$ and the measured gas flow $J_{measurement}$.

2. The method according to claim 1, wherein the at least one gas is selected from water vapor, oxygen, one of the water or oxygen isotopes, helium, hydrogen, or a mixture of at least two of said gases.

3. The method according to claim 1, wherein estimating the values of the parameters A and B includes at least an implementation of the following steps of:
   $a_1$) choosing initial values of the parameters A and B;
   $b_1$) calculating the estimation of the gas flow $J_{estim}(t)$;
   $c_1$) calculating the estimation error;
   $d_1$) when the estimation error is positive, decreasing the value of the parameter A and/or the value of the parameter B, and when the estimation error is negative, increasing the value of the parameter A and/or the value of the parameter B,
   wherein the implementation of steps $b_1$) to $d_1$) is successively repeated several times until a stabilization of the estimated values of the parameters A and B is achieved.

4. The method according to claim 3, wherein step $c_1$) includes the implementation of the following steps of:
   dividing $J_{estim}(t)$ and $J_{measurement}$ into several parts such that each of these parts corresponds to $J_{estim}(t)$ and $J_{measurement}$ for a time interval distinct from the time intervals of the other parts;
   for each of the parts of $J_{estim}(t)$ and $J_{measurement}$, calculating a parameter $$\mathit{ErrorJ}_{part\_i} = \int_{t \in part\_i} (J_{estim}(t) - J_{measurement}),$$

with part_i corresponding to the time interval of the corresponding parts of $J_{estim}(t)$ and $J_{measurement}$;

calculating parameters ErrorA and ErrorB, corresponding to the estimation errors of the parameters A and B respectively and forming together the estimation error, each of the parameters ErrorA and ErrorB being equal to a linear combination of the parameters $\mathit{ErrorJ}_{part\_i}$, and wherein step $d_1$) is implemented such that:
   when a value of the parameter ErrorA is positive, the value of the parameter A is decreased;
   when the value of the parameter ErrorA is negative, the value of the parameter A is increased;
   when a value of the parameter ErrorB is positive, the value of the parameter B is decreased; and
   when the value of the parameter ErrorB is negative, the value of the parameter B is increased.

5. The method according to claim 3, wherein the stabilization of the estimated values of the parameters A and B is achieved when the values of the parameters A and B include at least first six digits, in scientific notation, identical to those of the values of the parameters A and B obtained during the previous implementation of steps $b_1$) to $d_1$).

6. The method according to claim 1, wherein the values of the parameters A and B are decreased or increased by a variable pitch the value of which depends on previous decreases or increases in the values of the parameters A and B.

7. The method according to claim 1,
   wherein the estimation of the values of the parameters A and B is implemented several times by considering, at each of these estimations, different values of the parameter OffX and/or the parameter OffY, and
   wherein final values of the parameters A and B are chosen as being those for which a global error between the measured gas flow $J_{measurement}$ and the estimation of the gas flow $J_{estim}(t)$ is minimum among all the steps of estimating the values of the parameters A and B implemented.

8. The method according to claim 1, wherein,
   when a global error between the measured gas flow $J_{measurement}$ and the estimation of the gas flow $J_{estim}(t)$ reaches a minimum value at an instant $t_x$ and is higher than this minimum value after $t_x$, a new estimation of values of parameters $A_x$ and $B_x$, corresponding to the parameters A and B for $t > t_x$, is implemented,
   the values of the parameters $A_x$ and $B_x$ are iteratively estimated by decreasing an estimation error based on a difference, for $t > t_x$, between the estimation of the gas flow $J_{estim\_x}(t)$ calculated based on the estimated values of the parameters $A_x$ and $B_x$ and the measured gas flow $J_{measurement}$ from which is subtracted the estimation of the gas flow $J_{estim}(t)$ for $t < t_x$, with X an integer higher than 1, and
   the previously calculated parameters A and B are designated $A_1$ and $B_1$.

9. The method according to claim 1, wherein the measured gas flow $J_{measurement}$ is obtained from a measurement of a change over time of the partial pressure of the at least one gas in the second chamber.

10. The method according to claim 9, wherein,
   during the implementation of the steps of measuring the gas flow $J_{measurement}$ and estimating the values of the parameters A and B, the gas barrier layer is saturated with gas, and
   the measured gas flow $J_{measurement}$ corresponds to the pressure decrease of the at least one gas in the second chamber of the permeameter.

11. The method according to claim 10, further including,
after estimating the values of the parameters A and B,
calculating a stabilized gas flow J∞ such that J∞=A·B, or when an estimation of the values of the parameters $A_x$ and $B_x$ is implemented, calculating stabilized gas flows $J\infty_x$ such that $J\infty_x = A_x \cdot B_x$.

12. The method according to claim 9 further comprising:
depressurizing the first chamber and the second chamber relative to the at least one gas;

firstly implementing the method for estimating the gas flow such that a measured gas flow, designated $J_{degas\_measurement}$, corresponds to the pressure decrease of the at least one gas in the second chamber;

calculating an estimation of a gas flow $J_{degas\_estim}(t)$ from the last values of the parameters A and B previously estimated during the first implementation of the method for estimating the gas flow;

introducing the at least one gas into the first chamber such that the partial pressure of the at least one gas in the first chamber is higher than the partial pressure of the at least one gas in the second chamber; and secondly implementing the method for estimating the gas flow such that the measured gas flow $J_{measurement}$, corresponds to the pressure rise of the at least one gas in the second chamber, and during which the estimation of the values of the parameters A and B is performed by decreasing the estimation error based on a difference between an estimation of the gas flow $J_{perm\_estim}(t)$ and another gas flow $J_{perm\_measurement}$ such that $J_{perm\_measurement} = J_{measurement} - J_{degas\_estim}(t)$.

13. The method according to claim 12, wherein,
when a global error between the measured gas flow $J_{degas\_measurement}$ and the estimation of the gas flow $J_{degas\_estim}(t)$ is lower than a value of a first threshold $Y_{lower\_degas}$, the estimation of the gas flow $J_{degas\_estim}(t)$ is subtracted from the values of the measured gas flow $J_{measurement}$ during the second implementation of the method for estimating the gas flow, and when the global error between the measured gas flow $J_{degas\_measurement}$ and the estimation $J_{degas\_estim}(t)$ is higher than the value of a second threshold $Y_{upper\_degas}$, a last measured value of the gas flow $J_{degas\_measurement}$ or an average of several last measured values of the gas flow $J_{degas\_measurement}$ is subtracted from the values of the measured gas flow $J_{measurement}$ during the second implementation of the method for estimating the gas flow.

14. The method according to claim 12, further including,
after estimating the values of the parameters A and B during the second implementation of the method for estimating a gas flow, calculating a stabilized gas flow J∞ such that J∞=A·B, or when an estimation of the values of the parameters $A_x$ and $B_x$ is implemented during the second implementation of a method for estimating a gas flow, calculating a stabilized gas flows $J\infty_x$ such that $J\infty_x = A_x \cdot B_x$.

15. A device for estimating a permeation of a gas barrier layer, the device comprising:

a permeameter including first and second chambers separated from each other by the gas barrier layer, wherein the first chamber is filled with at least one gas and the second chamber is maintained in a low pressure regimen relative to said at least one gas;

a mass spectrometer provided in the second chamber of the permeameter; and processing circuitry configured to
calculate a gas flow $J_{measurement}$ in the second chamber based on a partial pressure of the at least one gas in the second chamber measured by the mass spectrometer as a function of time, estimate values of parameters A and B iteratively implemented by decreasing an estimation error based on a difference between an estimation of the gas flow $J_{estim}(t)$ and the measured gas flow $J_{measurement}$, wherein when the measured gas flow $J_{measurement}$ corresponds to a pressure rise of the at least one gas in the second chamber, the estimation of the gas flow $J_{estim}(t)$ is calculated according to the equation:

$$J_{estim}(t) = 2A \sum_{n=1}^{nmax} \left(\frac{B}{\pi(t-\mathit{OffX})}\right)^{\frac{1}{2}} \exp\left(\frac{-(2n+1)^2}{4B(t-\mathit{OffX})}\right) + \mathit{OffY},$$

when the measured gas flow $J_{measurement}$ corresponds to a pressure decrease of the at least one gas in the second chamber, the estimation of the gas flow $J_{estim}(t)$ is calculated according to the equation:

$$J_{estim}(t) = P_{init} - 2A \sum_{n=1}^{nmax} \left(\frac{B}{\pi(t-\mathit{OffX})}\right)^{\frac{1}{2}} \exp\left(\frac{-(2n+1)^2}{4B(t-\mathit{OffX})}\right) + \mathit{OffY},$$

and

OffX and OffY are relative integers, $P_{init}$ is an initial value of a measured partial pressure of the at least one gas in the second chamber, and $n_{max}$ is an integer higher than or equal to 1, and determine the permeation of the gas barrier layer based on the estimated values of the parameters A and B by calculating the difference between the estimation of the gas flow $J_{estim}(t)$ and the measured gas flow $J_{measurement}$.

\* \* \* \* \*